US010558029B2

(12) United States Patent
Leshem et al.

(10) Patent No.: US 10,558,029 B2
(45) Date of Patent: Feb. 11, 2020

(54) SYSTEM FOR IMAGE RECONSTRUCTION USING A KNOWN PATTERN

(71) Applicant: Scopio Labs Ltd., Tel Aviv (IL)

(72) Inventors: Ben Leshem, Tel Aviv (IL); Itai Hayut, Tel Aviv (IL); Erez Na'Aman, Tel Aviv (IL); Eran Small, Tel Aviv (IL)

(73) Assignee: Scopio Labs Ltd., Tel Aviv (IL)

( * ) Notice: Subject to any disclaimer, the term of this patent is extended or adjusted under 35 U.S.C. 154(b) by 89 days.

(21) Appl. No.: 15/795,150

(22) Filed: Oct. 26, 2017

(65) Prior Publication Data

US 2018/0120553 A1    May 3, 2018

Related U.S. Application Data

(60) Provisional application No. 62/413,727, filed on Oct. 27, 2016.

(51) Int. Cl.
*G16H 30/40* (2018.01)
*G02B 21/36* (2006.01)
(Continued)

(52) U.S. Cl.
CPC .......... *G02B 21/365* (2013.01); *G01N 21/17* (2013.01); *G01N 21/25* (2013.01); *G02B 21/14* (2013.01);
(Continued)

(58) Field of Classification Search
CPC ...... G02B 21/365; G02B 21/14; G02B 21/34; G02B 21/367; G16H 30/40; G01N 21/17; G01N 21/25
(Continued)

(56) References Cited

U.S. PATENT DOCUMENTS 5,982,534 A    11/1999   Pinkel et al.
6,430,309 B1    8/2002   Pressman et al.
(Continued)

FOREIGN PATENT DOCUMENTS

WO    WO-2015134924 A1    9/2015
WO    WO-2015179452 A1    11/2015
(Continued)

OTHER PUBLICATIONS

Anonymous: Computer multitasking—Wikipedia, https://en.wikipedia.org/wiki/Computermultitasking Accessed on Jan. 10, 2018.
(Continued)

*Primary Examiner* — Nguyen T Truong
(74) *Attorney, Agent, or Firm* — Wilson Sonsini Goodrich & Rosati

(57) ABSTRACT

Disclosed herein are systems and methods for constructing an image of a sample using a plurality of images acquired under multiple illumination conditions. In some cases, a microscope may include an image capture device, an illumination assembly, and a processor configured to acquire a plurality of images of a sample and a fiducial marker under a plurality of different illumination conditions and to reconstruct a high resolution image in response to the plurality of images. The disclosure also provides a method for generating a high resolution image of a sample comprising acquiring a plurality of images of a sample and a fiducial marker under a plurality of different illumination conditions and reconstructing the high resolution image in response to the plurality of images.

23 Claims, 18 Drawing Sheets

(51) Int. Cl.
*G01N 21/17* (2006.01)
*G01N 21/25* (2006.01)
*G02B 21/34* (2006.01)
*G02B 21/14* (2006.01)

(52) U.S. Cl.
CPC ........... *G02B 21/34* (2013.01); *G02B 21/367* (2013.01); *G16H 30/40* (2018.01)

(58) Field of Classification Search
USPC .......................................................... 348/79
See application file for complete search history.

(56) References Cited

U.S. PATENT DOCUMENTS

| | | | |
|---|---|---|---|
| 8,005,289 | B2 | 8/2011 | Dutta-Choudhury |
| 8,386,015 | B2 | 2/2013 | Kamen et al. |
| 9,103,784 | B1* | 8/2015 | Sivasankar ........ G01N 21/6404 |
| 2004/0263960 | A1 | 12/2004 | Obuchi |
| 2005/0052634 | A1 | 3/2005 | Sugihara et al. |
| 2006/0022114 | A1 | 2/2006 | Kennedy et al. |
| 2010/0141823 | A1* | 6/2010 | Tsunekawa ........... G06T 3/4053 348/333.12 |
| 2014/0118529 | A1 | 5/2014 | Zheng et al. |
| 2015/0054979 | A1 | 2/2015 | Ou et al. |
| 2015/0317508 | A1 | 11/2015 | Zheng et al. |
| 2016/0195705 | A1* | 7/2016 | Betzig .................... G02B 5/005 348/79 |
| 2017/0038574 | A1* | 2/2017 | Zhuang .............. G02B 21/0068 |
| 2018/0017774 | A1* | 1/2018 | Tomosugi .......... G01N 21/6458 |
| 2018/0149855 | A1* | 5/2018 | Chou .................... G02B 27/32 |

FOREIGN PATENT DOCUMENTS

| | | |
|---|---|---|
| WO | WO-2017081539 A1 | 5/2017 |
| WO | WO-2017081540 A1 | 5/2017 |
| WO | WO-2017081541 A1 | 5/2017 |
| WO | WO-2017081542 A2 | 5/2017 |
| WO | WO-2017081542 A3 | 7/2017 |

OTHER PUBLICATIONS

International Search Report and Written Opinion dated Feb. 28, 2017 for International PCT Patent Application No. IB-201601714.
International Search Report and Written Opinion dated Feb. 28, 2017 for International PCT Patent Application No. IB-201601715.
International Search Report and Written Opinion dated Apr. 20, 2017 for International PCT Patent Application No. IB-201601703.
International Search Report and Written Opinion dated May 9, 2017 for International PCT Patent Application No. IB-201601725.
Tian, et al., Quantitative phase recovery from asymmetric illumination on an LED array microscope, Progress in Biomedical Optics and Imaging, SPIE—International Society for Optical Engineering, Bellingham, WA, US, Mar. 11, 2015, 9336:93360A-93360A.

* cited by examiner

SYSTEM FOR IMAGE RECONSTRUCTION USING A KNOWN PATTERN

CROSS-REFERENCE

This patent application claims priority to U.S. Prov. App. Ser. No. 62/413,727, filed on Oct. 27, 2016, entitled "Iterative and Non-Iterative Processes for High Resolution Image Generation", the entire disclosure of which is incorporated herein by reference.

BACKGROUND

Prior methods and apparatus of generating high resolution images with computational microscopy can be less than ideal in at least some respects. For example, the amount of time to compute a high resolution image can be somewhat longer than would be ideal. Also, the quality of the high resolution image obtained can be less than ideal or may not be known in at least some instances. In addition, the number of different illuminations used to generate a high resolution computational image can result in the image acquisition time being somewhat longer than would be ideal.

In light of the above, improved methods and apparatus for computational microscopy are needed which decrease the amount of time used to generate computational images, can provide verification of the quality of the generated images, and decrease the number of different illumination conditions used to generate the computational images.

SUMMARY

A microscope configured to acquire a plurality of images of a sample and a fiducial marker can provide improved high resolution images. Imaging the fiducial marker with the sample can provide additional information which can be used to provide improved high resolution images of the sample. The fiducial marker may comprise a known periodic pattern, and spatial frequency information in the sample image can be used to generate the high resolution image in response to the image of the fiducial marker present in the sample image. The plurality of images may comprise low resolution images, and the high resolution image can be generated in response to the plurality of low resolution images. The high resolution image can be constructed iteratively and the image of the fiducial maker can be used to assess convergence of the high resolution image. Alternatively, the high resolution image can be constructed non-iteratively and information from the image of the fiducial marker used as input to the non-iterative high resolution image reconstruction. Because the image of the fiducial marker provides additional information, fewer illumination conditions may be used to generate the plurality of images, thereby decreasing the number of images and time to acquire the images. Also, the additional information provided by the fiducial marker can decrease the number of computations and computation time used to generate the high resolution image. Information related to the fiducial present in the high resolution image can be used to assess the quality of the high resolution image.

In one aspect, the present disclosure provides a microscope for generating a high resolution image of a sample, said microscope comprises: an illumination assembly; and image capture device; a fiducial marker imaged with said image capture device; and a processor coupled to the illumination assembly and the image capture device. In some embodiments, the processor is configured with instructions to: acquire a plurality of images under a plurality of different illumination conditions, wherein said sample and the fiducial marker are present within the plurality of images, and reconstruct the high resolution image of the sample in response to the fiducial marker and the plurality of images.

In some embodiments, the fiducial marker is present in each of the plurality of images.

In some embodiments, the plurality of images each comprises a resolution and the high resolution image comprises a resolution greater than said resolution of said each plurality of images.

In some embodiments, the fiducial marker comprises a predetermined pattern.

In some embodiments, the fiducial marker comprises a predetermined periodic pattern comprising a predetermined spatial frequency.

In some embodiments, the fiducial marker comprises predetermined spatial frequency, and the processor is configured with instructions to reconstruct the high resolution image in response to the predetermined spatial frequency of the fiducial marker.

In some embodiments, the fiducial marker comprises features within a range from about 0.1 to 10 times a size of the smallest features from the sample present in the high-resolution image and optionally wherein the range is from about 0.2 to about 5 times the size of the smallest features.

In some embodiments, each of said plurality of images is within a field of view of said image capture device.

In some embodiments, the processor is configured with instructions to reconstruct said high resolution image in response to a frequency of said fiducial marker. The processor may be configured with instructions to reconstruct said high resolution image in response to a plurality of frequencies of said fiducial marker. The processor may be configured with instructions to reconstruct said high resolution image in response to the plurality of frequencies of said fiducial marker in each of the plurality of images.

In some embodiments, the processor is configured with instructions to reconstruct said high resolution image in response to a phase of said fiducial marker in said reconstructed image. The processor may be configured with instructions to reconstruct said high resolution image in response to a phase difference between a phase of the fiducial marker and a phase of the fiducial marker in the reconstructed image.

In some embodiments, said fiducial marker is disposed between said sample and an illumination source.

In some embodiments, said fiducial marker is disposed between said sample and the image capture device. Said fiducial marker may be located between said sample and an objective lens of said illumination device.

In some embodiments, said fiducial marker comprises a physical object disposed adjacent to said sample.

In some embodiments, said sample and said fiducial marker are disposed on a microscope slide.

In some embodiments, said fiducial marker has been fabricated on a microscope slide.

In some embodiments, said fiducial marker is disposed on a region of a microscope slide and at least a portion of said fiducial marker is not obscured by said sample.

In some embodiments, said fiducial marker is located on a microscope slide supporting the sample.

In some embodiments, said fiducial marker is disposed on a coverslip.

In some embodiments, said fiducial marker is visible in a brightfield image.

In some embodiments, said fiducial marker comprises a predetermined shape and intensity profile.

In some embodiments, the processor is configured with instructions to determine an attribute value of said fiducial marker in said plurality of images and generate a reconstruction parameter if the attribute value is outside a predetermined range.

In some embodiments, said attribute value is selected from the group consisting of a phase value, a frequency value, and an intensity value.

In some embodiments, said attribute value corresponds to a presence or weight of a frequency of said pattern in said reconstructed high resolution image.

In some embodiments, said attribute value of said fiducial marker is obtained by performing a transformation to the frequency domain on one or more of the plurality of low resolution images.

In some embodiments, said transformation comprises a Fourier-related transformation or an orthogonal transformation.

In some embodiments, said transformation is selected from the group consisting of a Hadamard transformation, transformation, a discrete cosine transformation, a discrete Fourier transformation, a Walsh-Hadamard transformation, a Haar transformation, and a Slant transformation.

In some embodiments, the processor is configured with instructions to: generate a first reconstructed image using said reconstruction parameter, determine that said first reconstructed image is not of a desired quality, adjust said reconstruction parameter, and generate a second reconstructed image.

In some embodiments, said reconstruction parameter is adjusted until said attribute value is determined to be within said predetermined range.

In some embodiments, said different illumination conditions comprise conditions selected from the group consisting of different illumination angles, different illumination wavelengths, different illumination patterns, different illumination durations, different illumination intensities, and different illumination positions.

In some embodiments, the processor is configured to reconstruct the high resolution image from the plurality of images without iterations.

In some embodiments, the processor is configured to reconstruct the high resolution image from the plurality of images with iterations.

In some embodiments, the image capture device comprises a plurality of imaging sensors.

In another aspect, the present disclosure provides a method for generating a high resolution image of a sample, said method comprising: acquiring a plurality of images of the sample and a fiducial maker under a plurality of different illumination conditions, wherein the sample and the fiducial marker are present in the plurality of images; and reconstructing the high resolution image of the sample in response to the fiducial maker and the plurality of images.

In some embodiments, the fiducial marker is present in each of the plurality of images.

In some embodiments, the plurality of images each comprises a resolution and the high resolution image comprises a resolution greater than said resolution of said plurality of images.

In some embodiments, the fiducial marker comprises a predetermined pattern.

In some embodiments, the fiducial marker comprises a predetermined periodic pattern comprising a predetermined spatial frequency.

In some embodiments, the fiducial marker comprises predetermined spatial frequency, and the processor is configured with instructions to reconstruct the high resolution image in response to the predetermined spatial frequency of the fiducial marker.

In some embodiments, the fiducial marker comprises features within a range from about 0.1 to 10 times a size of the smallest features from the sample present in the high-resolution image and optionally wherein the range is from about 0.2 to about 5 times the size of the smallest features.

In some embodiments, each of said plurality of images is within a field of view of said image capture device.

In some embodiments, the processor is configured with instructions to reconstruct said high resolution image in response to a frequency of said fiducial marker. The processor may be configured with instructions to reconstruct said high resolution image in response to a plurality of frequencies of said fiducial marker. The processor may be configured with instructions to reconstruct said high resolution image in response to the plurality of frequencies of said fiducial marker in each of the plurality of images.

In some embodiments, the processor is configured with instructions to reconstruct said high resolution image in response to a phase of said fiducial marker in said reconstructed image. The processor may be configured with instructions to reconstruct said high resolution image in response to a phase difference between a phase of the fiducial marker and a phase of the fiducial marker in the reconstructed image.

In some embodiments, said fiducial marker is disposed between said sample and an illumination source.

In some embodiments, said fiducial marker is disposed between said sample and the image capture device. Said fiducial marker may be located between said sample and an objective lens of said illumination device.

In some embodiments, said fiducial marker comprises a physical object disposed adjacent to said sample.

In some embodiments, said sample and said fiducial marker are disposed on a microscope slide.

In some embodiments, said fiducial marker has been fabricated on a microscope slide.

In some embodiments, said fiducial marker is disposed on a region of a microscope slide and at least a portion of said fiducial marker is not obscured by said sample.

In some embodiments, said fiducial marker is located on a microscope slide supporting the sample.

In some embodiments, said fiducial marker is disposed on a coverslip.

In some embodiments, said fiducial marker is visible in a brightfield image.

In some embodiments, said fiducial marker comprises a predetermined shape and intensity profile.

In some embodiments, the method further comprises determining an attribute value of said fiducial marker in said plurality of images and generating a reconstruction parameter if the attribute value is outside a predetermined range.

In some embodiments, said attribute value is selected from the group consisting of a phase value, a frequency value, and an intensity value.

In some embodiments, said attribute value corresponds to a presence or weight of a frequency of said pattern in said reconstructed high resolution image.

In some embodiments, said attribute value of said fiducial marker is obtained by performing a transformation to the frequency domain on one or more of the plurality of low resolution images.

In some embodiments, said transformation comprises a Fourier-related transformation or an orthogonal transformation.

In some embodiments, said transformation is selected from the group consisting of a Hadamard transformation, transformation, a discrete cosine transformation, a discrete Fourier transformation, a Walsh-Hadamard transformation, a Haar transformation, and a Slant transformation.

In some embodiments, the step of reconstruction comprises: generating a first reconstructed image using said reconstruction parameter, determining that said first reconstructed image is not of a desired quality, adjusting said reconstruction parameter, and generating a second reconstructed image.

In some embodiments, said reconstruction parameter is adjusted until said attribute value is determined to be within said predetermined range.

In some embodiments, the determining whether said first reconstructed image is of desired quality is based on a level of sharpness of said first reconstructed image.

In some embodiments, said different illumination conditions comprise conditions selected from the group consisting of different illumination angles, different illumination wavelengths, different illumination patterns, different illumination durations, different illumination intensities, and different illumination positions.

In some embodiments, the processor is configured to reconstruct the high resolution image from the plurality of images without iterations.

In some embodiments, the processor is configured to reconstruct the high resolution image from the plurality of images with iterations.

In some embodiments, the processor is configured to reconstruct the high resolution image from the plurality of images without iterations.

In some embodiments, the plurality of images is acquired with an image capture device. The image capture device may comprise a plurality of imaging sensors.

In another aspect, the disclosure provides a tangible medium comprising instructions of a computer program configured to perform the method of any one of the preceding claims.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "Fig." herein), of which:

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Disclosed embodiments provide microscopes and methods that use one or more cameras to provide high-resolution images of a sample which may be located on a stage. In various embodiments, the microscope may use images of the sample captured under a plurality of illumination conditions. For example, the plurality of illumination conditions may include different illumination angles. In one aspect of the disclosure, the microscope may identify, in the captured images, multiple occurrences of the sample corresponding to the plurality of illumination conditions. The microscope may estimate a shift between the occurrences and determine a degree in which the microscope is out of focus. This aspect of the disclosure is described in detail with reference to FIGS. 2-4. In another aspect of the disclosure, the microscope may capture multiple images of the sample under each illumination condition, aggregate image data from these images, and construct a high-resolution image from the image data. In one example, the microscope may aggregate the image data in the Fourier plane and then use inverse Fourier transform to reconstruct the high-resolution image. This aspect of the disclosure is described in detail with reference to FIGS. 5-10. Another aspect of the disclosure provides a microscope including a processor configured with instructions to acquire a plurality of images of a sample and a fiducial marker in proximity to the sample under a plurality of illumination conditions and to subsequently reconstruct a high resolution image. This aspect of the disclosure is described in detail with reference to FIGS. 11-13.

Figure 1:
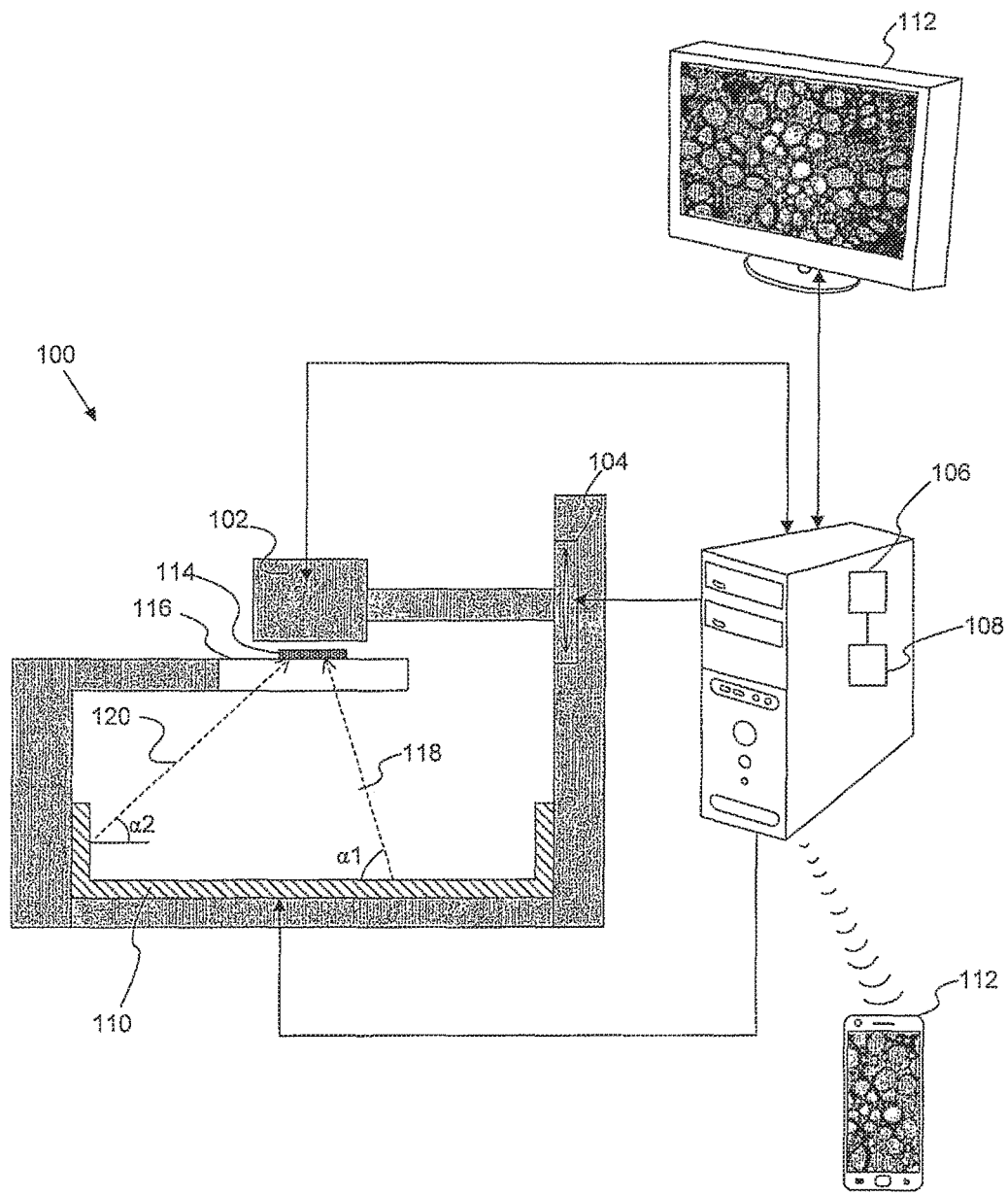
FIG. 1 is a diagrammatic representation of an exemplary microscope, consistent with the disclosed embodiments.

FIG. 1 is a diagrammatic representation of a microscope 100 consistent with the exemplary disclosed embodiments. The term "microscope" refers to any device or instrument for magnifying an object which is smaller than easily observable by the naked eye, i.e., creating an image of an object for a user where the image is larger than the object. One type of microscope may be an "optical microscope" that uses light in combination with an optical system for magnifying an object. An optical microscope may be a simple microscope having one or more magnifying lens. Another type of microscope may be a "computational microscope" that includes an image sensor and image-processing algorithms to enhance or magnify the object's size or other properties. The computational microscope may be a dedicated device or created by incorporating software and/or hardware with an existing optical microscope to produce high-resolution digital images. As shown in FIG. 1, microscope 100 includes an image capture device 102, a focus actuator 104, a processor 106 connected to memory 108, an illumination assembly 110, and a user interface 112. An example usage of microscope 100 may be capturing images of a sample 114 mounted on a stage 116 located within the field-of-view (FOV) of image capture device 102, processing the captured images, and presenting on user interface 112 a magnified image of sample 114.

Image capture device 102 may be used to capture images of sample 114. In this specification, the term "image capture device" includes a device that records the optical signals entering a lens as an image or a sequence of images. The optical signals may be in the near-infrared, infrared, visible, and ultraviolet spectrums. Examples of an image capture device include a CCD camera, a CMOS camera, a photo sensor array, a video camera, a mobile phone equipped with a camera, etc. Some embodiments may include only a single image capture device 102, while other embodiments may include two, three, or even four or more image capture devices 102. In some embodiments, image capture device 102 may be configured to capture images in a defined field-of-view (FOV). Also, when microscope 100 includes several image capture devices 102, image capture devices 102 may have overlap areas in their respective FOVs. Image capture device 102 may have one or more image sensors (not shown in FIG. 1) for capturing image data of sample 114. In other embodiments, image capture device 102 may be configured to capture images at an image resolution higher than 10 Megapixels, higher than 12 Megapixels, higher than 15 Megapixels, or higher than 20 Megapixels. In addition, image capture device 102 may also be configured to have a pixel size smaller than 5 micrometers, smaller than 3 micrometers, or smaller than 1.6 micrometer.

In some embodiments, microscope 100 includes focus actuator 104. The term "focus actuator" refers to any device capable of converting input signals into physical motion for adjusting the relative distance between sample 114 and image capture device 102. Various focus actuators may be used, including, for example, linear motors, electrostrictive actuators, electrostatic motors, capacitive motors, voice coil actuators, magnetostrictive actuators, etc. In some embodiments, focus actuator 104 may include an analog position feedback sensor and/or a digital position feedback element. Focus actuator 104 is configured to receive instructions from processor 106 in order to make light beams converge to form a clear and sharply defined image of sample 114 and/or a fiducial marking in proximity to sample 114, as described herein. In the example illustrated in FIG. 1, focus actuator 104 may be configured to adjust the distance between, e.g., sample 114 and image capture device 102 by moving image capture device 102. However, in other embodiments, focus actuator 104 may be configured to adjust the distance by moving stage 116, or by moving both image capture device 102 and stage 116. In some cases, movement of focus actuator 104 may permit the collection of a focused image of sample 114. In other cases, movement of focus actuator 104 may permit the collection of a focused image of a fiducial marking disposed in proximity to sample 114. In certain cases, movement of focus actuator 104 may permit the collection of a focused image of sample 114 and a fiducial marking disposed in proximity to sample 114.

Microscope 100 may also include processor 106 for controlling the operation of microscope 100 according to the disclosed embodiments. Processor 106 may comprise various components and devices for performing logic operations on one or more inputs of image data and other data according to stored or accessible software instructions providing desired functionality. For example, processor 106 may include a central processing unit (CPU), a memory, support circuits, digital signal processors, integrated circuits, cache memory, or any other types of devices for image processing and analysis such as graphic processing units (GPUs). The CPU may comprise any number of microcontrollers or microprocessors configured to process and/or collect image data from image sensors. For example, the CPU may include any type of single- or multi-core processor, mobile device microcontroller, etc. Various processors may be used, including, for example, processors available from manufacturers such as Intel®, AMD®, etc. and may include various architectures (e.g., x86 processor, ARM®, etc.). The support circuits may be any number of circuits generally well known in the art, including cache, power supply, clock and input-output circuits.

In some embodiments, processor 106 may be associated with memory 108 used for storing software that, when executed by processor 106, controls the operation of microscope 100. In addition, memory 108 may also store electronic data associated with operation of microscope 100 such as, for example, captured or generated images of sample 114. In one instance, memory 108 may be integrated into the processor 106. In another instance, memory 108 may be separate from processor 106. Specifically, memory 108 may refer to multiple structures or computer-readable storage mediums located at processor 106 or at a remote location, such as a cloud server. Memory 108 may comprise any number of random access memories, read only memories, flash memories, disk drives, optical storage, tape storage, removable storage and other types of storage.

Microscope 100 may include illumination assembly 110. The term "illumination assembly" refers to any device or system capable of projecting light to illuminate sample 114 and/or a fiducial marking disposed in proximity to sample 114. Illumination assembly 110 may include any number of light sources, such as light emitting diodes (LEDs), lasers, and lamps configured to emit light. In one embodiment, illumination assembly 110 may include only a single light source. Alternatively, illumination assembly 110 may include two, four, sixteen, or even more than a hundred light sources organized in an array or a matrix. In some embodiments, illumination assembly 110 may include or use one or more light sources located at a surface parallel to sample 114 and/or a fiducial marking in proximity to sample 114, as described herein. In other embodiments, illumination assembly 110 may include or use one or more light sources located at a surface perpendicular or at an angle to sample 114 and/or a fiducial marking in proximity to sample 114, as described herein.

In addition, illumination assembly 110 may be configured to illuminate sample 114 and/or a fiducial marking disposed in proximity to sample 114 in a series of different illumination conditions. In one example, illumination assembly 110 may include a plurality of light sources arranged in different illumination angles, such as a two-dimensional arrangement of light sources. In this case, the different illumination conditions may include different illumination angles. For example, FIG. 1 depicts a beam 118 projected from a first illumination angle $\alpha_1$, and a beam 120 projected from a second illumination angle $\alpha_2$. In some embodiments, first illumination angle $\alpha_1$ and second illumination angle $\alpha_2$ have the same value but opposite sign. In other embodiments, first illumination angle $\alpha_1$ may be separated from second illumination angle $\alpha_2$. However, both angles originate from points within the acceptance angle of the optics. In another example, illumination assembly 110 may include a plurality of light sources configured to emit light in different wavelengths. In this case, the different illumination conditions may include different wavelengths. In yet another example, illumination assembly 110 may configured to use a number of light sources at predetermined times. In this case, the different illumination conditions may include different illumination patterns. Accordingly and consistent with the present disclosure, the different illumination conditions may be selected from a group including: different durations, different intensities, different positions, different illumination angles, different illumination patterns, different wavelengths, or any combination thereof.

Consistent with disclosed embodiments, microscope 100 may include, be connected with, or in communication with (e.g., over a network or wirelessly, e.g., via Bluetooth) user interface 112. The term "user interface" refers to any device suitable for presenting a magnified image of sample 114 or any device suitable for receiving inputs from one or more users of microscope 100. FIG. 1 illustrates two examples of user interface 112. The first example is a smartphone or a tablet wirelessly communicating with processor 106 over a Bluetooth, cellular connection or a Wi-Fi connection, directly or through a remote server. The second example is a personal computer display physically connected to processor 106. In some embodiments, user interface 112 may include user output devices, including, for example, a display, tactile device, speaker, etc. In other embodiments, user interface 112 may include user input devices, including, for example, a touchscreen, microphone, keyboard, pointer devices, cameras, knobs, buttons, etc. With such input devices, a user may be able to provide information inputs or commands to microscope 100 by typing instructions or information, providing voice commands, selecting menu options on a screen using buttons, pointers, or eye-tracking capabilities, or through any other suitable techniques for communicating information to microscope 100. User interface 112 may be connected (physically or wirelessly) with one or more processing devices, such as processor 106, to provide and receive information to or from a user and process that information. In some embodiments, such processing devices may execute instructions for responding to keyboard entries or menu selections, recognizing and interpreting touches and/or gestures made on a touchscreen, recognizing and tracking eye movements, receiving and interpreting voice commands, etc.

Microscope 100 may also include or be connected to stage 116. Stage 116 includes any horizontal rigid surface where sample 114 may be mounted for examination. Stage 116 may include a fiducial marking (e.g., etched or deposited thereon), as described herein. Stage 116 may include a mechanical connector for retaining a slide containing sample 114 in a fixed position. The mechanical connector may use one or more of the following: a mount, an attaching member, a holding arm, a clamp, a clip, an adjustable frame, a locking mechanism, a spring or any combination thereof. In some embodiments, stage 116 may include a translucent portion or an opening for allowing light to illuminate sample 114 and/or a fiducial marking disposed in proximity to sample 114, as described herein. For example, light transmitted from illumination assembly 110 may pass through sample 114 and towards image capture device 102. In some embodiments, stage 116 and/or sample 114 may be moved using motors or manual controls in the XY plane to enable imaging of multiple areas of sample 114 and/or a fiducial marking disposed in proximity to sample 114, as described herein.

Figure 2A:
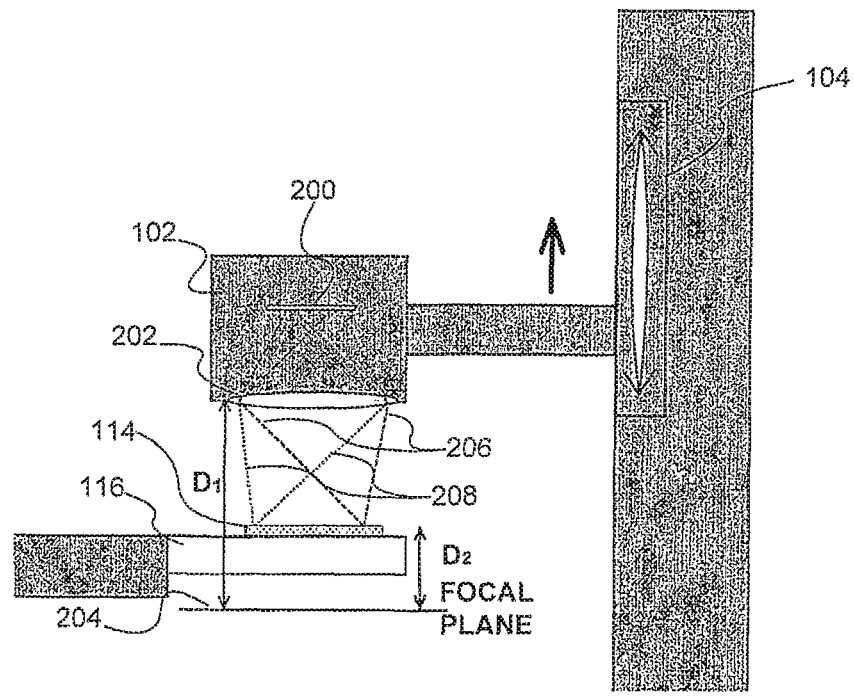
FIG. 2A is a diagrammatic representation of the optical paths of two beam pairs when the microscope of FIG. 1 is out of focus, consistent with the disclosed embodiments.
Figure 2B:
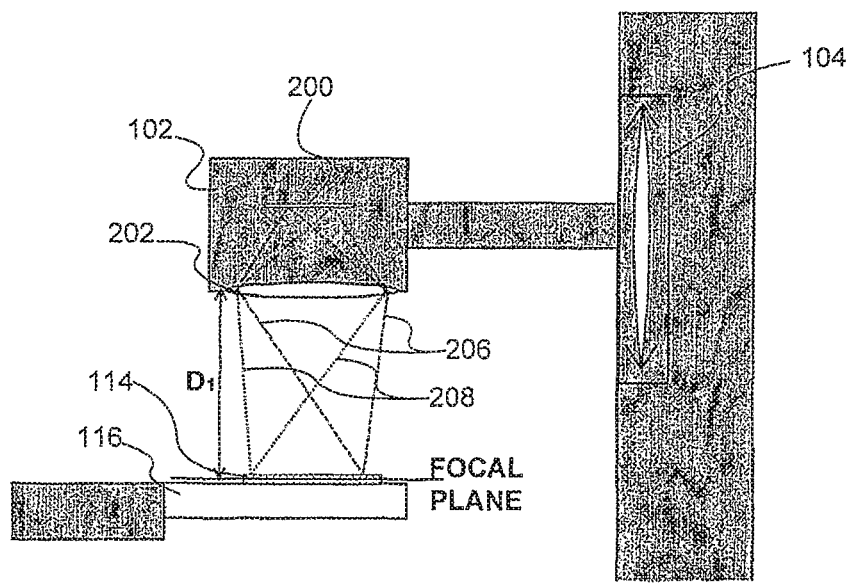
FIG. 2B is a diagrammatic representation of the optical paths of two beam pairs when the microscope of FIG. 1 is in focus, consistent with the disclosed embodiments.

FIGS. 2A and 2B depict a closer view of microscope 100 in two cases. Specifically, FIG. 2A illustrates the optical paths of two beams pairs when microscope 100 is out of focus (e.g., configured to collect in-focus images of sample 114 and/or a fiducial marking disposed in proximity to sample 114), and FIG. 2B illustrates the optical paths of two beams pairs when microscope 100 is in focus (e.g., configured to collect out-of-focus images of sample 114 and/or a fiducial marking disposed in proximity to sample 114).

As shown in FIGS. 2A and 2B, image capture device 102 includes an image sensor 200 and a lens 202. In microscopy, lens 202 may be referred to as an objective lens of microscope 100. The term "image sensor" refers to a device capable of detecting and converting optical signals into electrical signals. The electrical signals may be used to form an image or a video stream based on the detected signals. Examples of image sensor 200 may include semiconductor charge-coupled devices (CCD), active pixel sensors in complementary metal-oxide-semiconductor (CMOS), or N-type metal-oxide-semiconductor (NMOS, Live MOS). The term "lens" may refer to a ground or molded piece of glass, plastic, or other transparent material with opposite surfaces either or both of which are curved, by means of which light rays are refracted so that they converge or diverge to form an image. The term "lens" also refers to an element containing one or more lenses as defined above, such as in a microscope objective. The lens is positioned at least generally transversely of the optical axis of image sensor 200. Lens 202 may be used for concentrating light beams from sample 114 and directing them towards image sensor 200. In some embodiments, image capture device 102 may include a fixed lens or a zoom lens.

When sample 114 and/or a fiducial marking, as described herein, is located at a focal-plane 204, the image projected from lens 202 is completely focused. The term "focal-plane" is used herein to describe a plane that is perpendicular to the optical axis of lens 202 and passes through the lens's focal point. The distance between focal-plane 204 and the center of lens 202 is called the focal length and is represented by D1. In some cases, sample 114 may not be completely flat, and there may be small differences between focal-plane 204 and various regions of sample 114. Accordingly, the distance between focal-plane 204 and sample 114 or a region of interest (ROI) of sample 114 (and/or a fiducial marking in proximity to sample 114, as described herein) is marked as D2. The distance D2 corresponds with the degree in which an image of sample 114, an image of ROI of sample 114, and/or a fiducial marking in proximity to sample 114, as described herein, is out of focus. For example, distance D2 may be between 0 and about 3 mm. In some embodiments, D2 may be greater than 3 mm. When distance D2 equals to zero, the image of sample 114 (or the image of ROI of sample 114, and/or a fiducial marking in proximity to sample 114, as described herein) is completely focused. In contrast, when D2 has a value other than zero, the image of sample 114 (or the image of ROI of sample 114, and/or a fiducial marking in proximity to sample 114, as described herein) is out of focus.

FIG. 2A depicts a case where the image of sample 114, and/or a fiducial marking in proximity to sample 114, as described herein, is out of focus. For example, the image of sample 114 may be out of focus when the beams of light received from sample 114 do not converge on image sensor 200. FIG. 2A depicts a beams pair 206 and a beams pair 208. Neither pair converges on image sensor 200. For the sake of simplicity, the optical paths below sample 114 are not shown. Consistent with the present disclosure, beams pair 206 may correspond with beam 120 projected from illumination assembly 110 at illumination angle $\alpha_2$, and beams pair 208 may correspond with beam 118 projected from illumination assembly 110 at illumination angle $\alpha_1$. In addition, beams pair 206 may concurrently hit image sensor 200 with beams pair 208. The term "concurrently" in this context means that image sensor 200 has recorded information associated with two or more beams pairs during coincident or overlapping time periods, either where one begins and ends during the duration of the other, or where a later one starts before the completion of the other. In other embodiments, beams pair 206 and beams pair 208 may sequentially contact image sensor 200. The term "sequentially" means that image sensor 200 has started recording information associated with, for example, beam pair 206 after the completion of recording information associated with, for example, beam pair 208.

As discussed above, D2 is the distance between focal-plane 204 and sample 114, and/or a fiducial marking in proximity to sample 114, as described herein, and it corresponds with the degree in which sample 114, and/or a fiducial marking, is out of focus. In one example, D2 may have a value of 50 micrometers. Focus actuator 104 is configured to change distance D2 by converting input signals from processor 106 into physical motion. In some embodiments, in order to focus the image of sample 114, and/or a fiducial marking in proximity to sample 114, focus actuator 104 may move image capture device 102. In this example, focus actuator 104 may move image capture device 102 some number of micrometers, such as 50 micrometers, up to focus the image of sample 114 and/or a fiducial marking in proximity to sample 114. In other embodiments, focus actuator 104 may move stage 116 down in order to focus the image of sample 114 and/or a fiducial marking. Therefore, in this example, instead of moving image capture device 102 50 micrometers up, focus actuator 104 may move stage 116 50 micrometers down.

FIG. 2B illustrates a case where the image of sample 114, and/or a fiducial marking in proximity to sample 114, as described herein, is in focus. In this case, both beam pairs 206 and 208 converge on image sensor 200, and distance D2 is equal to zero. In other words, focusing the image of sample 114 (or the image of ROI of sample 114 and/or a fiducial marking in proximity to sample 114, as described herein) may require adjusting the relative distance between image capture device 102 and sample 114. The relative distance may be represented by D1-D2, such that when distance D2 equals to zero, the relative distance between image capture device 102 and sample 114 and/or a proximate fiducial marking is equal to distance D1, which means that the image of sample 114 and/or the fiducial marking is focused. In the embodiment illustrated in FIGS. 2A and 2B, lens 202 has a fixed focal length, i.e., distance D1 is constant. Therefore, the missing parameter needed to focus the image of sample 114 and/or a proximate fiducial marking is distance D2. The present disclosure provides a microscope and a method for determining the value of distance D2.

Figure 3A:
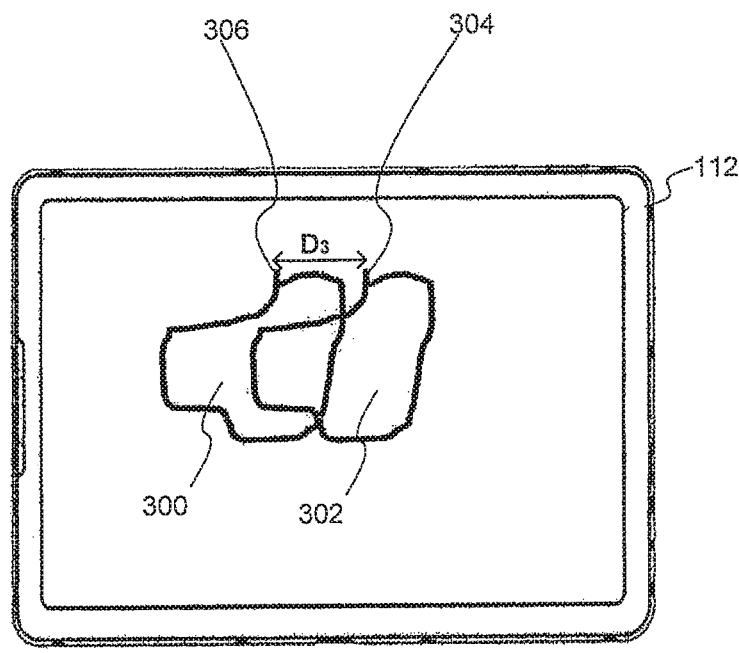
FIG. 3A is a diagrammatic representation of an exemplary image shown on a display when the microscope of FIG. 1 is out of focus, consistent with the disclosed embodiments.
Figure 3B:
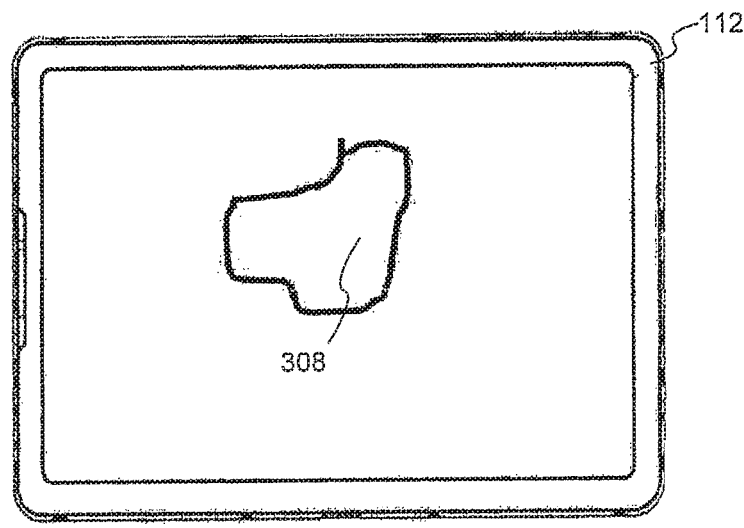
FIG. 3B is a diagrammatic representation of an exemplary image shown on a display when the microscope of FIG. 1 is in focus, consistent with the disclosed embodiments.

FIG. 3A and FIG. 3B illustrate how microscope 100 may determine the value of distance D2 using images acquired under a plurality of different illumination conditions. Specifically, FIG. 3A illustrates an exemplary image (or two images overlaid on top of each other) shown on user interface 112 when the image of sample 114 and/or a fiducial marking in proximity to sample 114, as described herein, is out of focus, and FIG. 3B illustrates an exemplary image shown user interface 112 when the image of sample 114 and/or a proximate fiducial marking is in focus.

FIG. 3A shows user interface 112 displaying information obtained from image sensor 200 that corresponds with the case illustrated in FIG. 2A. As shown, user interface 112 displays a first representation 300 of sample 114 and/or a proximate fiducial marking and a second representation 302 of sample 114 and/or a proximate fiducial marking. Each representation corresponds to a different illumination condition. For example, first representation 300 may correspond to first illumination angle $\alpha_1$, and second representation 302 may correspond to the second illumination angle $\alpha_2$. In one embodiment, both first representation 300 and second representation 302 are displayed together as part of a captured image because the light from the first illumination angle $\alpha_1$ may concurrently hit image sensor 200 with the light projected the second illumination angle $\alpha_2$. In another embodiment, first representation 300 is captured as a first image and second representation 302 is captured as a second image. Both images may be overlaid on top of each other and shown as a single image or used for calculations together.

In some embodiments, processor 106 may be configured to identify the relative positions of the two (or more) representations using at least one common image feature. The common image feature may be a feature of sample 114 or a fiducial marking in proximity to sample 114, as described herein. As used herein, the term "image feature" refers to an identifiable element in a digital image, such as a line, a point, a spot, an edges, a region of similar brightness, a similar shape, an area of the image, etc. or other distinguishing characteristic of the pixels that comprise the image of sample 114. The changes between the two (or more) representations may be distinguishable with the naked eye and/or with the aid of image analysis algorithms that include feature detection or use a region of interest, which may be part, or all of the image, as the input features, such as, Marr-Hildreth algorithm, scale-invariant feature transform (SIFT) algorithm, speeded up robust features (SURF) algorithm, Digital image correlation (DIC) algorithm, cross correlation etc. As shown in FIG. 3A, both first representation 300 and second representation 302 include a sharp protrusion on the upper side of the representation. Accordingly, processor 106 may identify a first occurrence 304 of the sharp protrusion and a second occurrence 306 of the sharp protrusion as a common image feature of sample 114. Consistent with the present disclosure, first occurrence 304 may be associated the first illumination angle $\alpha_1$ and second occurrence 306 may be associated with the second illumination angle $\alpha_2$.

After identifying multiple occurrences of at least one image feature of sample 114 associated with a plurality of illumination conditions, processor 106 may estimate an amount of shift between the occurrences. In FIG. 3A, the shift between first occurrence 304 and second occurrence 306 is represented by D3. The shift between first occurrence 304 and second occurrence 306 may be measured by counting the number of pixels between two occurrences of the same one or more image features. In theory, measured values of shift D3 originate from comparing multiple image features in the first and second representations and should be substantially identical. However, as often happens in real-life applications, there may be a significant variation in the measured values of shift D3 when estimating shifts of a plurality of image features. These variations may be caused by a tilt of microscope 100, a non-flat sample, field curvature of lens 202, and more. Therefore, in order to estimate the shift D3 between first representation 300 and second representation 302, processor 106 may apply statistical calculations on the measured values. The statistical calculations may include one or more of the following operations: a mean, a median, an average, a mode, a percentile or a standard deviation. Processor 106 may additionally apply these statistical calculations when determining a plurality of shift values or a vector shift when using more than two illumination conditions, such as, more than two illumination angles. The same analysis may apply when a fiducial marking, or feature thereof, is used as a common element between the first and second representations, as described herein.

In one embodiment, after estimating shift D3 between first representation 300 and second representation 302, processor 106 may determine distance D2 (the distance between focal-plane 204 and sample 114, and/or a fiducial marking in proximity to sample 114, as described herein) using the distance between the illumination source(s) L, the distance between the illumination source plane and current focal plane Z and D3 in order to calculate the distance D2. In one example the distance D2 may be calculated using the following linear equation:

$$D2 = D3 \times (Z/L)$$

In order for processor 106 to reduce the distance between sample 114 and focal-plane 204, processor 106 may also determine the direction of the required adjustment. For example, in some cases focal-plane 204 may be below sample 114 and/or a fiducial marking in proximity to sample 114, as described herein (as illustrated in FIG. 2A), and processor 106 would need to increase the relative distance between image capture device 102 and sample 114, and/or a proximate fiducial marking, to focus the image. But in other cases focal-plane 204 may be above sample 114 and/or a proximate fiducial marking and processor 106 may need to decrease the relative distance between image capture device 102 and sample 114 and/or the proximate fiducial marking to focus the image. In one embodiment, processor 106 may determine the direction of the required adjustment using a two-step process. For example, assuming D2 has a value of 1 mm, processor 106 may instruct focus actuator 104 to move image capture device 102 0.3 mm up, and check if the focus of the image had improved. If it did improve, processor 106 may instruct focus actuator 104 to continue moving image capture device 102 up for additional 0.7 mm. But if it did not improve, processor 106 may instruct focus actuator 104 to move image capture device 102 down 1.3 mm. In another embodiment, processor 106 may determine the direction of the required adjustment using a one-step process such as, for example, by purposefully introducing a known separation between sample 114 and/or a fiducial marking in proximity to sample 114, as described herein, and the focal-plane 204. The known separation may correspond with a known shift, and a change to the known shift may indicate the size and direction of the actual shift D3. In another embodiment, processor 106 may determine the direction of the required adjustment using a one-step process such as, for example, by measuring the direction of the shift of features between object images 300 and 302 and using the knowledge of the illumination conditions used, to understand if sample 114 and/or a fiducial marking in proximity to sample 114, as described herein, is above or below the focal plane.

FIG. 3B depicts user interface 112 displaying information obtained from image sensor 200 that corresponds with the case illustrated in FIG. 2B. As shown, user interface 112 displays a representation 308 of sample 114 and/or a fiducial marking in proximity to sample 114, as described herein. In this example, user interface 112 displays a single representation because the image of sample 114 and/or a proximate fiducial marking is in focus. That is, first occurrence 304 and second occurrence 306 were merged to representation 308 after the processor 106 adjusted the relative distance between image capture device 102 and sample 114 and/or a proximate fiducial marking.

In some embodiments, processor 106 may determine that the quality of the image is not sufficient. For example, the level of sharpness associated with an image of sample 114 and/or a fiducial marking in proximity to sample 114, as described herein, may be below a predefined threshold. The level of sharpness may vary due to, for example, unintentional movement of microscope 100, a change of the ROI of sample 114, and more. To improve the quality of the image, processor 106 may refocus microscope 100. In addition, processor 106 may determine a plurality of shift values that correspond with a plurality of portions of a field of view of image capture device 102 to determine three-dimensional information. The three-dimensional information may include, for example, tilt information between microscope 100 and sample 114, a 3D shape of an object, and/or the field curvature of lens 202. Processor 106 may use tilt information when reconstructing the image of sample 114 and/or a fiducial marking in proximity to sample 114 to improve the sharpness of the image. Additional examples regarding the reconstruction of the image of sample 114 and/or a fiducial marking in proximity to sample 114 is provided below with reference to FIGS. 5-10.

Figure 4:
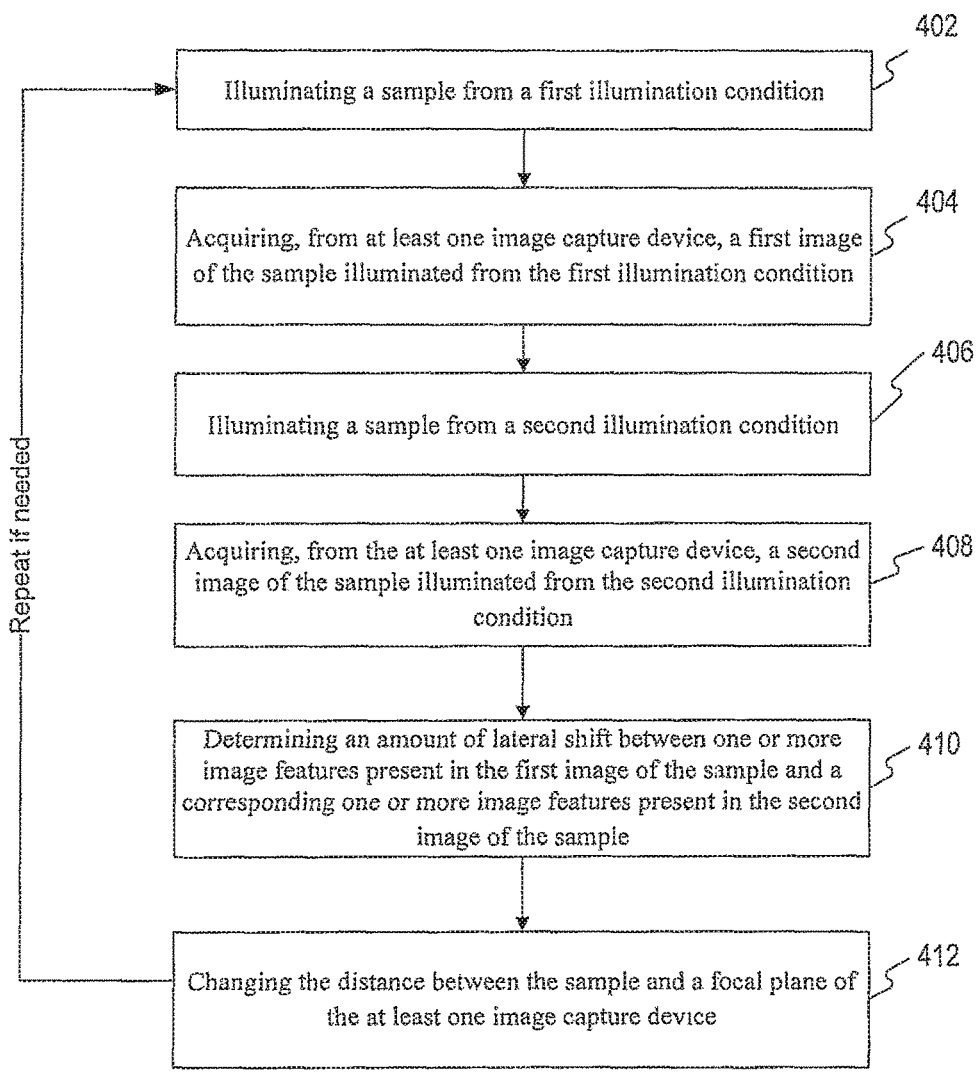
FIG. 4 is a flowchart showing an exemplary process for focusing an image of a sample using images acquired under a plurality of illumination conditions, consistent with the disclosed embodiments.

FIG. 4 is a flowchart showing an exemplary process 400 for focusing an image of sample 114 and/or a fiducial marking in proximity to sample 114, as described herein, using two images captured when sample 114 is illuminated under two illumination conditions. Process 400, however, may be adapted to focus an image of sample 114 using a single image captured when sample 114 is illuminated under two illumination conditions, or using one or more images when sample 114 is illuminated under more than two illumination conditions. The steps of process 400 may be performed by an autofocus microscope. The term "autofocus microscope" refers to any device for magnifying sample 114 with the capability to focus the image of sample 114 (or the image of ROI of sample 114 and/or a fiducial marking in proximity to sample 114, as described herein) in an automatic or semiautomatic manner. In the following description, reference is made to certain components of microscope 100 for purposes of illustration. It will be appreciated, however, that other implementations are possible and that other components may be utilized to implement the example process.

At step 402, processor 106 may cause illumination assembly 110 to illuminate sample 114 under a first illumination condition. At step 404, processor 106 may acquire, from image capture device 102, a first image of sample 114 and/or a fiducial marking in proximity to sample 114, as described herein, illuminated under the first illumination condition. In some embodiments, processor 106 may cause illumination assembly 110 to illuminate sample 114 and/or a proximate fiducial marking using a single light source located within a numerical aperture of image capture device 102. Alternatively, processor 106 may cause illumination assembly 110 to illuminate sample 114 and/or a proximate fiducial marking using a plurality of light sources located within the numerical aperture of image capture device 102.

At step 406, processor 106 may cause illumination assembly 110 to illuminate sample 114 and/or a proximate fiducial marking under a second illumination condition different from the first illumination condition. Next, at step 408, processor 106 may acquire, from image capture device 102, a second image of sample 114 and/or a proximate fiducial marking illuminated under the second illumination condition. In some embodiments, the illumination conditions may include at least one of: different illumination angles, different illumination patterns, different wavelengths, or a combination thereof. For example, the illumination conditions may include a first illumination angle and a second illumination angle symmetrically located with respect to an optical axis of image capture device 102. Alternatively, the illumination conditions may include a first illumination angle and a second illumination angle asymmetrically located with respect to an optical axis of image capture device 102. Alternatively, the illumination conditions may include a first illumination angle and a second illumination angle within the numerical aperture of image capture device 102. In the example depicted in FIG. 1, first illumination angle $\alpha_1$ is greater than second illumination angle $\alpha_2$, so the first illumination angle and the second illumination angle are asymmetrically located with respect to an optical axis of image capture device 102.

At step 410, processor 106 may determine an amount of shift D3 between one or more image features present in the first image of sample 114 and a corresponding one or more image features present in the second image of sample 114. Alternatively, processor 106 may determine a amount of shift D3 between an image feature associated with a fiducial marking, or a feature thereof, disposed in proximity to sample 114 in a first image of sample 114 and/or the fiducial marking and a corresponding image feature present in a second image of sample 114 and/or the fiducial marking. In some embodiments, processor 106 may determine a plurality of shift values based on multiple image features and calculate an overall shift associated with shift D3. For example, the overall shift may be a mean, a median, a mode of the plurality of shift values. In other embodiments, processor 106 may determine a size of the distance change based on a magnitude of shift D3. In addition, processor 106 may also determine a direction of the distance change based on a direction of shift D3, or by purposely introducing a known separation between the sample and the focal plane. As discussed above, in some cases, focal-plane 204 may be below sample 114 and/or a fiducial marking in proximity to sample 114, as described herein (as illustrated in FIG. 2A), and in other cases, focal-plane 204 may be above sample 114 and/or a proximate fiducial marking. These different cases may require a different direction of the distance change to focus microscope 100. In some embodiments, processor 106 may calculate a distance from focal-plane 204 to sample 114 and/or a proximate fiducial marking based on the shift (e.g., shift D3 in the lateral direction).

At step 412, processor 106 may, where the amount of determined shift D3 is non-zero, cause focus actuator 104 to change distance D2 between sample 114 and/or a proximate fiducial marking and focal-plane 204. As discussed above, 104 may move image capture device 102 and/or stage 116 to adjust distance D2 between sample 114 and/or a proximate fiducial marking and focal-plane 204. In some embodiments, processor 106 may cause focus actuator 104 to reduce the distance between sample 114 and/or a proximate fiducial marking and focal-plane 204 to substantially zero, for example, as illustrated in FIG. 2B. In some embodiments, when focus actuator 104 changes distance D2 in a first direction (e.g., up), processor 106 may determine that the amount of shift D3 has increased after the change in the first direction, and cause focus actuator 104 to change the distance in a second direction (e.g., down).

In some embodiments, processor 106 may repeat steps 402 to 410 to determine an amount of a new shift after adjusting distance D2 between sample 114 and/or a proximate fiducial marking and focal-plane 204. If the amount of the new shift is still non-zero, or above a predefined threshold, Processor 106 may cause focus actuator 104 to change again distance D2 between sample 114 and/or a proximate fiducial marking and focal-plane 204. In some embodiments, processor 106 may readjust distance D2 between sample 114 and/or a proximate fiducial marking and focal-plane 204 until shift D3 would be substantially zero or below the predefined threshold. When the amount of the new shift is below a predetermined threshold, processor 106 may store the amount of determined shift for future focus compensation calculations. After completing process 400, microscope 100 is completely focused. Thereafter, and according to another aspect of the disclosure, microscope 100 may acquire a plurality of focused images to generate a high-resolution image of sample 114. As shown in FIG. 1 and described herein, the high-resolution image of sample 114 may, for example, be sent to a display (e.g., a screen or phone), stored in memory, sent for further processing, or sent over a network.

In some embodiments, processor 106 may use the determined distance D2 to perform calculations for computational correction of focus along with physical motion stage 116 or without causing stage 116 to move. Furthermore, in some embodiments, stage 116 and/or sample 114 may be moved using motors or manual controls in the XY plane to enable imaging of multiple areas of sample 114 and/or a fiducial marking in proximity to sample 114, as described herein.

There are several known methods in the field of computational imaging processing for producing a high-resolution image of a sample from a set of low-resolution images. One of these methods is, for example, ptychography. These methods may use an iterative process in order to compute the high-resolution image in a way that the reconstructed image in each iteration is compared to a pre-iteration high-resolution image, and the difference between them serves as the convergence condition. The present disclosure describes microscopes and methods for producing a high-resolution image from a set of low resolution images taken with different illumination conditions, but does not require iterations as used by the known methods. Therefore, the disclosed microscopes and methods enable decreasing the computation time needed to reconstruct the high-resolution image.

Consistent with the present disclosure, processor 106 may acquire images at a first image resolution and generate a reconstructed image of sample 114 having a second (enhanced) image resolution. The term "image resolution" is a measure of the degree to which the image represents the fine details of sample 114. For example, the quality of a digital image may also be related to the number of pixels and the range of brightness values available for each pixel. In some embodiments, generating the reconstructed image of sample 114 is based on images having an image resolution lower than the enhanced image resolution. The enhanced image resolution may have at least 2 times, 5 times, 10 times, or 100 times more pixels than the lower image resolution images. For example, the first image resolution of the captured images may be referred to hereinafter as low resolution and may have a value of less than 2 megapixels, less than 25 megapixels, or greater than 25 megapixels; between 2 megapixels and 25 megapixels or between 10 megapixels and 20 megapixels; or of about 15 megapixels. Whereas, the second image resolution of the reconstructed image may be referred to hereinafter as high-resolution and may have a value higher than 40 megapixels, higher than 100 megapixels, higher than 500 megapixels, or higher than 1000 megapixels.

Figure 5:
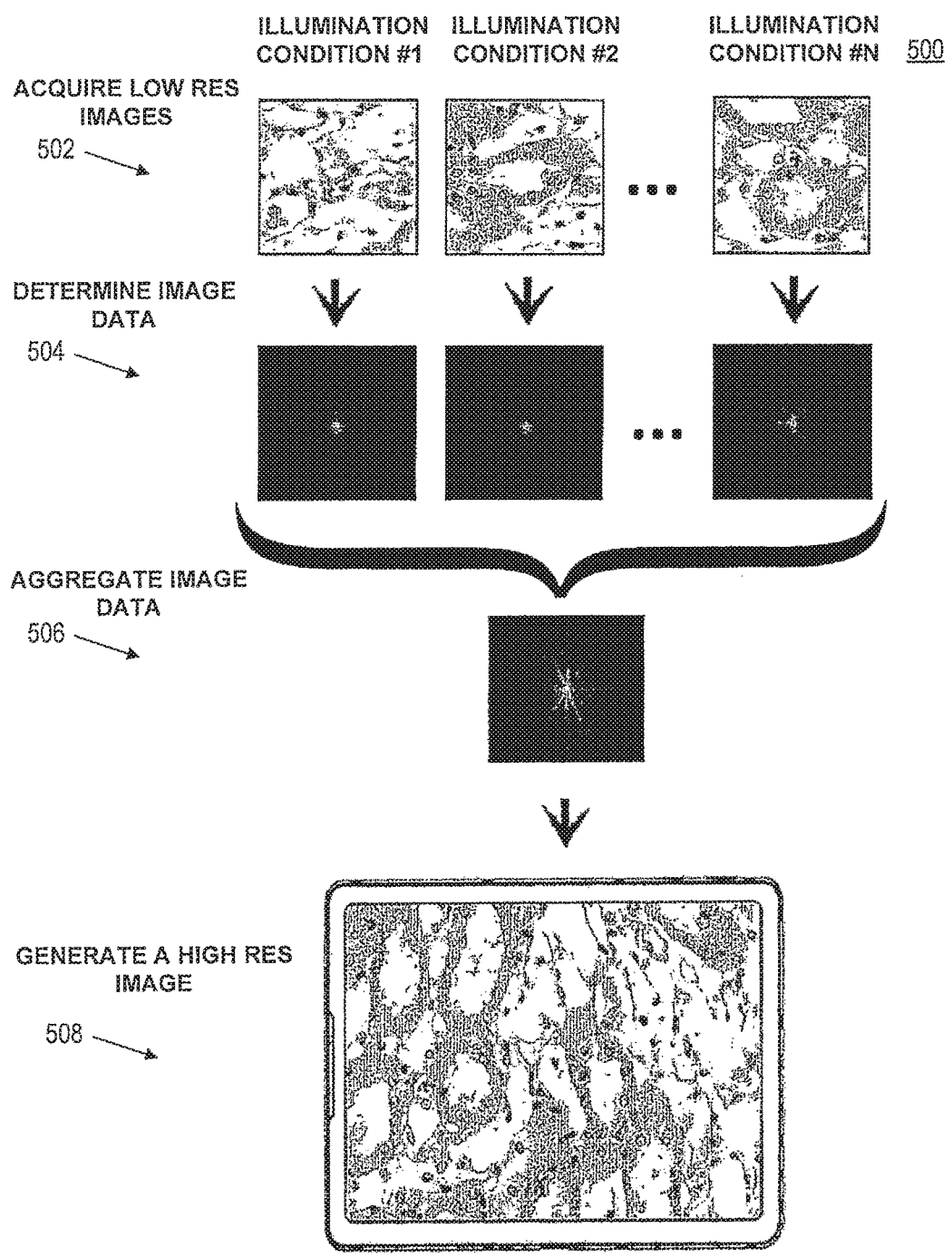
FIG. 5 is a representation of an exemplary process for constructing an image of a sample using images acquired under a plurality of illumination conditions, consistent with disclosed embodiments.

FIG. 5 is an illustration of an exemplary process 500 for reconstructing an image of sample 114, consistent with disclosed embodiments. At step 502, processor 106 may acquire from image capture device 102 a plurality of low resolution images of sample 114 and/or a fiducial marking in proximity to sample 114, as described herein. The plurality of images includes at least one image for each illumination condition. As mentioned above, the different illumination conditions may include at least one of: different illumination angles, different illumination patterns, different wavelengths, or a combination thereof. In some embodiments, the total number (N) of the plurality of different illumination conditions is between 2 to 10, between 5 to 50, between 10 to 100, between 50 to 1000, or more than 1000.

At step 504, processor 106 may determine image data of sample 114 and/or a proximate fiducial marking associated with each illumination condition. For example, processor 106 may apply a Fourier transform on images acquired from image capture device 102 to obtain Fourier transformed images. The Fourier transform is an image processing tool which is used to decompose an image into its sine and cosine components. The input of the transformation may be an image in the normal image space (also known as real-plane), while the output of the transformation may be a representation of the image in the frequency domain (also known as a Fourier-plane). Consistent with the present disclosure, the output of a transformation, such as the Fourier transform, is also referred to as "image data." Alternatively, processor 106 may use other transformations, such as a Laplace transform, a Z transform, a Gelfand transform, or a Wavelet transform. In order to rapidly and efficiently convert the captured images into images in the Fourier-plane, processor 106 may use a Fast Fourier Transform (FFT) algorithm to compute the Discrete Fourier Transform (DFT) by factorizing the DFT matrix into a product of sparse (mostly zero) factors.

At step 506, processor 106 may aggregate the image data determined from images captured under a plurality of illumination conditions to form a combined complex image. One way for processor 106 to aggregate the image data is by locating in the Fourier-plane overlapping regions in the image data, for example, by comparing common image features of sample 114 and/or a proximate fiducial marking, as described herein. Another way for processor 106 to aggregate the image data is by determining the intensity and phase for the acquired low-resolution images per illumination condition. In this way, the image data, corresponding to the different illumination conditions, does not necessarily include overlapping regions. By eliminating or reducing the amount of overlap needed, this method has a great advantage in reducing the number of illumination conditions needed in order to reconstruct an image with a certain resolution, and therefore increasing the acquisition speed of the image information. FIGS. 6A-6F illustrate different configurations of microscope 100 for determining phase information under a variety of illumination conditions. Intensity and phase information may be associated with a common image feature of sample 114 and/or a proximate fiducial marking, as described herein.

At step 508, processor 106 may generate a reconstructed high-resolution image of sample 114. For example, processor 106 may apply the inverse Fourier transform to obtain the reconstructed image. In one embodiment, depicted in FIG. 5, the reconstructed high-resolution image of sample 114 may be shown on a display (e.g., user interface 112). In another embodiment, the reconstructed high-resolution image of sample 114 may be used to identify at least one element of sample 114 in the reconstructed image. The at least one element of sample 114 may include any organic or nonorganic material identifiable using a microscope. Examples of the at least one element include, but are not limited to, biomolecules, whole cells, portions of cells such as various cell components (e.g., cytoplasm, mitochondria, nucleus, chromosomes, nucleoli, nuclear membrane, cell membrane, Golgi apparatus, lysosomes), cell-secreted components (e.g., proteins secreted to intercellular space, proteins secreted to body fluids, such as serum, cerebrospinal fluid, urine), microorganisms, and more. In some embodiments, the reconstructed image may be used in the following procedures: blood cell recognition, identification of chromosomes and karyotypes, detection of parasitic infections, identification of tissues suspected as malignant, and more.

Figure 7:
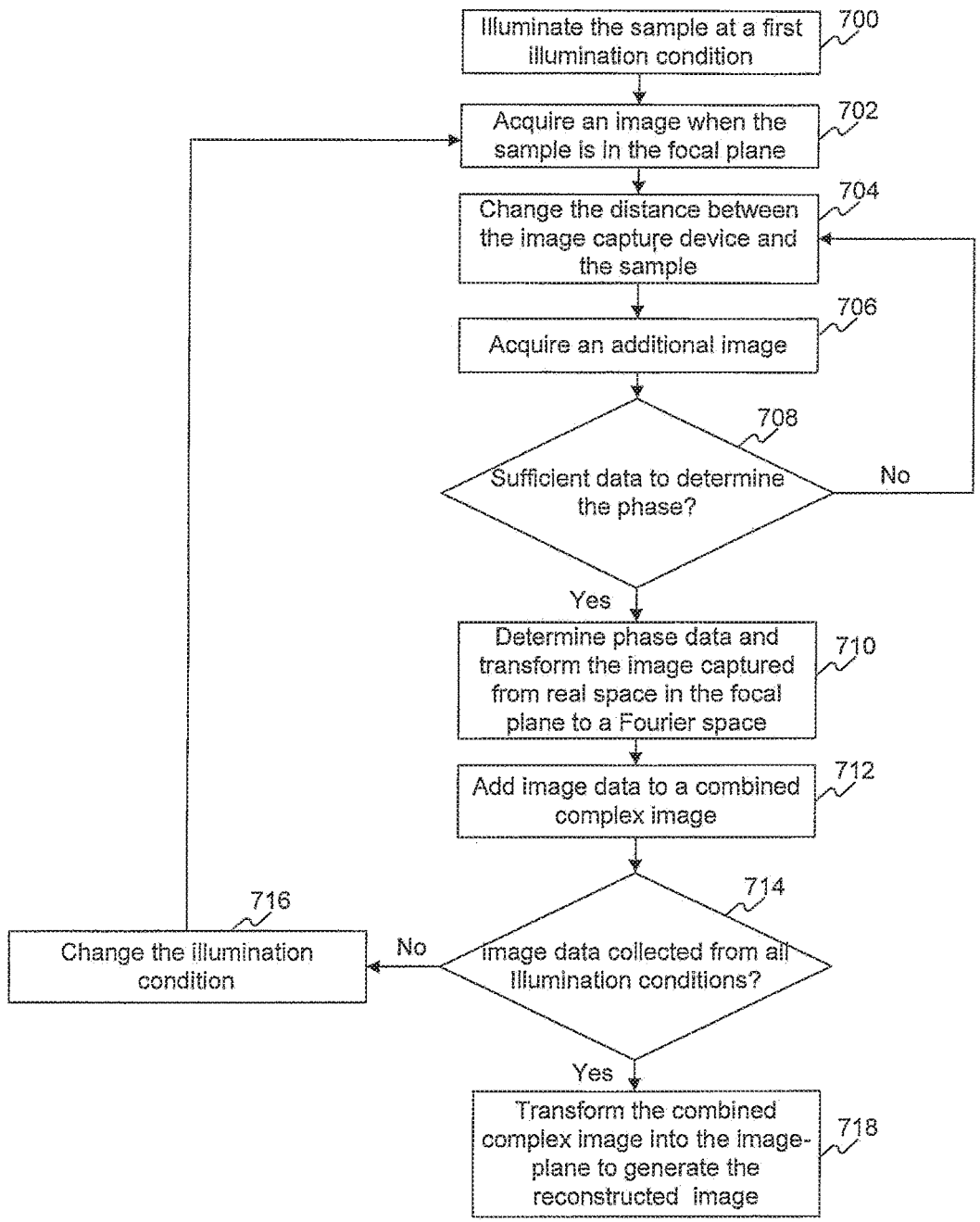
FIG. 7 is a flow diagram showing the implementation of the process of FIG. 5 using the configuration of FIG. 6A, consistent with the disclosed embodiments.

The present disclosure provides several ways to determine the phase information under each illumination condition. According to one embodiment that may be implemented in the configuration of FIG. 6A, microscope 100 may include illumination assembly 110, focus actuator 104, lens 202, and image sensor 200. In this embodiment, processor 106 may acquire a group of images from different focal-planes for each illumination condition. Therefore, processor 106 may use the information from the different focal-planes to determine the phase information under each illumination condition. FIG. 7 describes a detailed example process of how processor 106 may use the configuration of FIG. 6A to generate the reconstructed high-resolution image of sample 114.

Figure 6A:
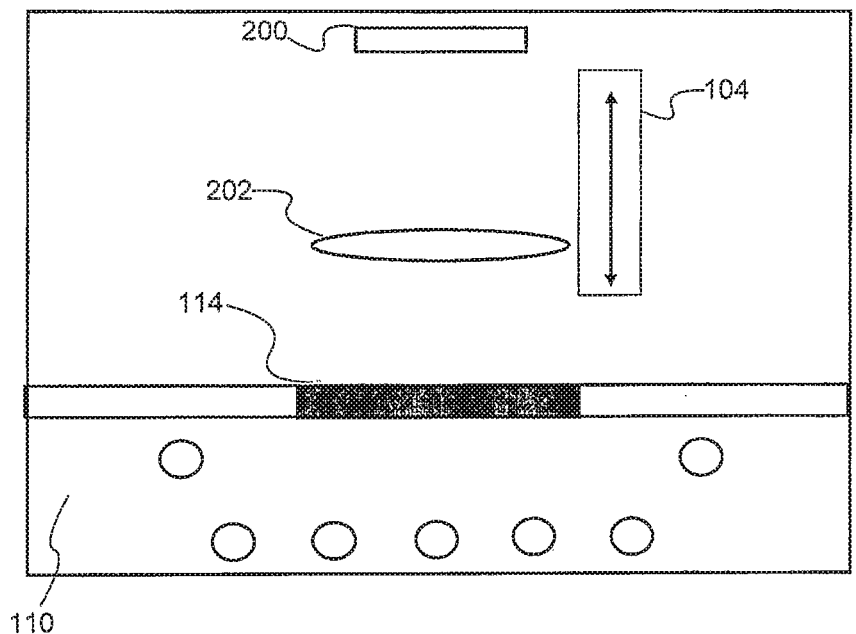
FIG. 6A is a diagrammatic representation of a configuration for determining phase information of a sample under a plurality of illumination conditions, consistent with the disclosed embodiments.
Figure 6B:
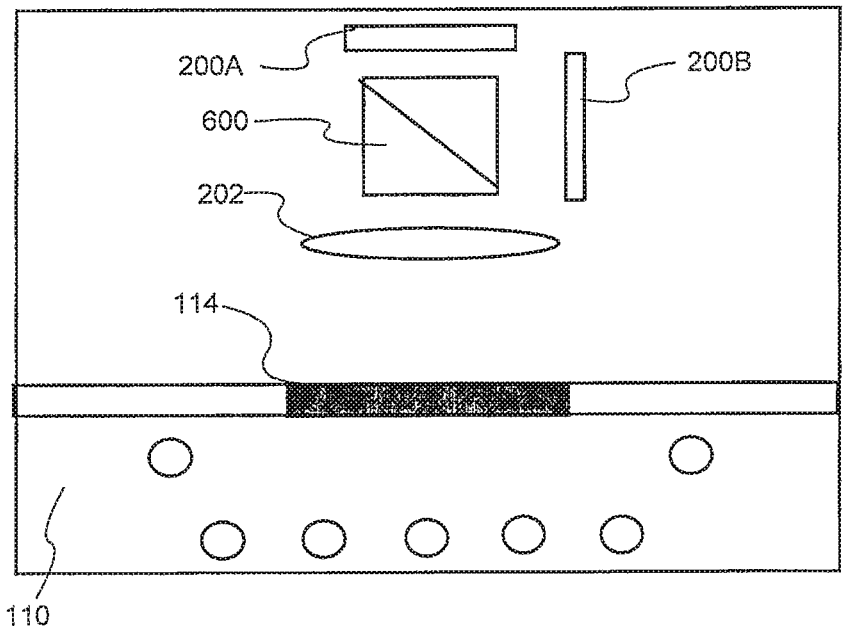
FIG. 6B is a diagrammatic representation of another configuration for determining phase information of a sample under a plurality of illumination conditions, consistent with the disclosed embodiments.

According to another embodiment that may be implemented in the configuration of FIG. 6B, microscope 100 may include illumination assembly 110, lens 202, a beam splitter 600, a first image sensor 200A, and a second image sensor 200B. In this embodiment, first image sensor 200A and second image sensor 200B may capture different types of images, and processor 106 may combine the information from first image sensor 200A and second image sensor 200B to determine the phase information under each illumination condition. In one example, image sensor 200A may capture Fourier-plane images and second image sensor 200B may capture real-plane images. Accordingly, processor 106 may acquire, for each illumination condition, a Fourier-plane image from first image sensor 200A and a real-plane image from second image sensor 200B. Therefore, processor 106 may combine information from the Fourier-plane image and the real-plane image to determine the phase information under each illumination condition. In another example, image sensor 200A may be configured to capture focused images and second image sensor 200B is configured to capture unfocused images. It is also possible that additional sensors may be added. For example, 3 different sensors may be configured to capture images in 3 different focal planes.

Figure 6C:
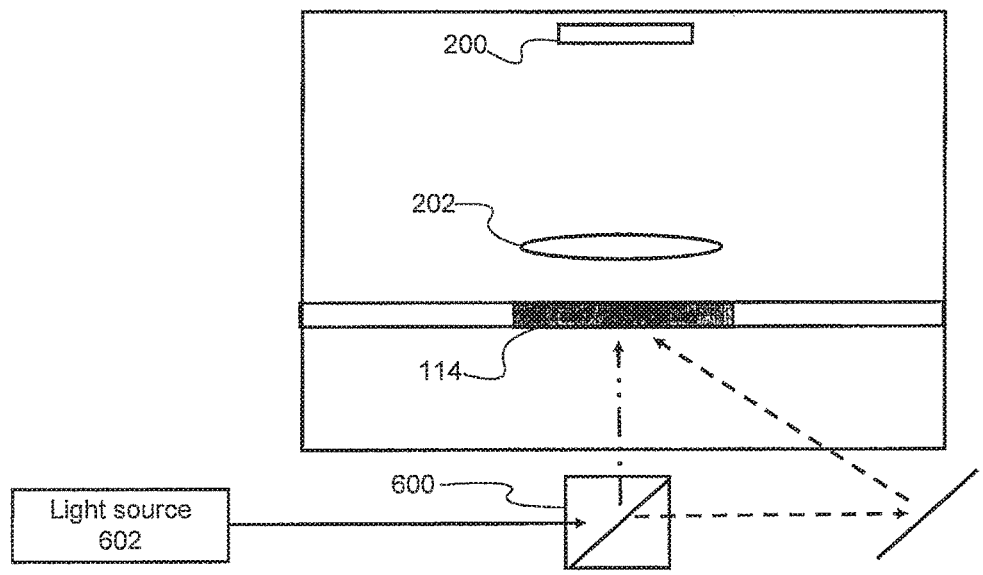
FIG. 6C is a diagrammatic representation of another configuration for determining phase information of a sample under a plurality of illumination conditions, consistent with the disclosed embodiments.
Figure 6D:
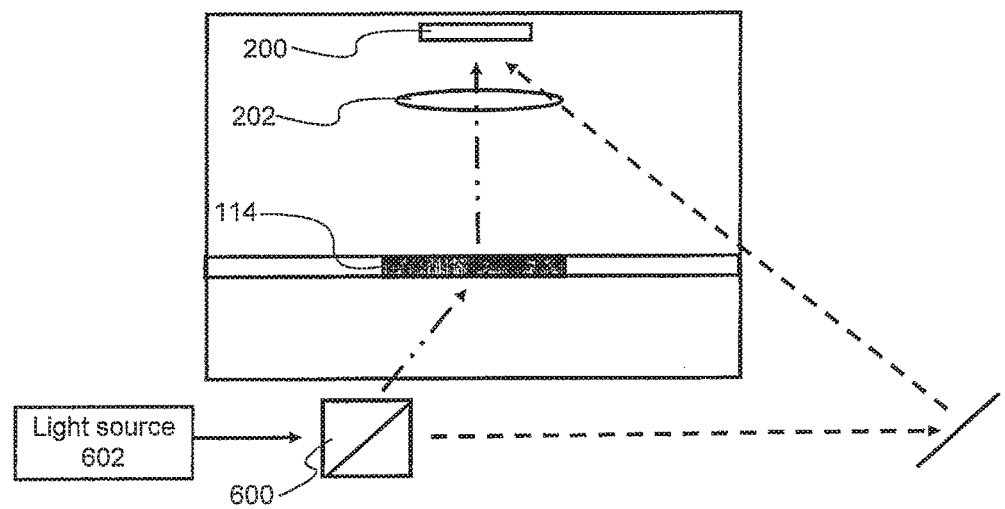
FIG. 6D is a diagrammatic representation of another configuration for determining phase information of a sample under a plurality of illumination conditions, consistent with the disclosed embodiments.

According to another embodiment that may be implemented in the configurations of FIG. 6C and FIG. 6D, microscope 100 may include a light source 602, a beam splitter 600, lens 202, and image sensor 200. In this embodiment, light source 602 may project a light beam (coherent or at least partially coherent) towards beam splitter 600, the beam splitter generates two light beams that travel through two different optical paths and create an interference pattern. In the configuration of FIG. 6C, the interference pattern is created on sample 114 and/or a fiducial marking in proximity to sample 114, as described herein, and in FIG. 6D, the interference pattern is created on image sensor 200. In the case presented in FIG. 6D, processor 106 may identify, for each illumination condition, the interference pattern between the two light beams traveling through the different optical paths, and determine, from the interference pattern, the phase associated with each illumination condition.

Figure 6E:
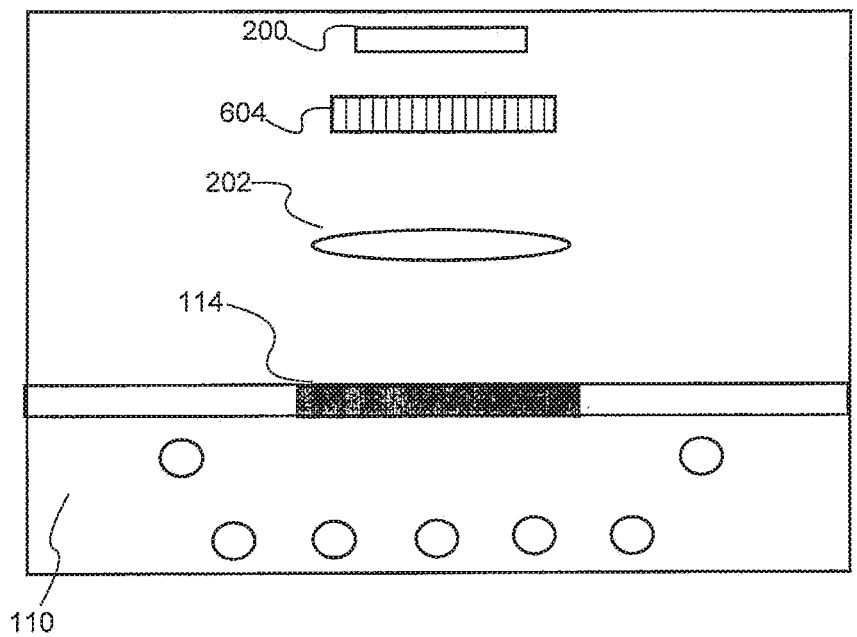
FIG. 6E is a diagrammatic representation of another configuration for determining phase information of a sample under a plurality of illumination conditions, consistent with the disclosed embodiments.
Figure 6F:
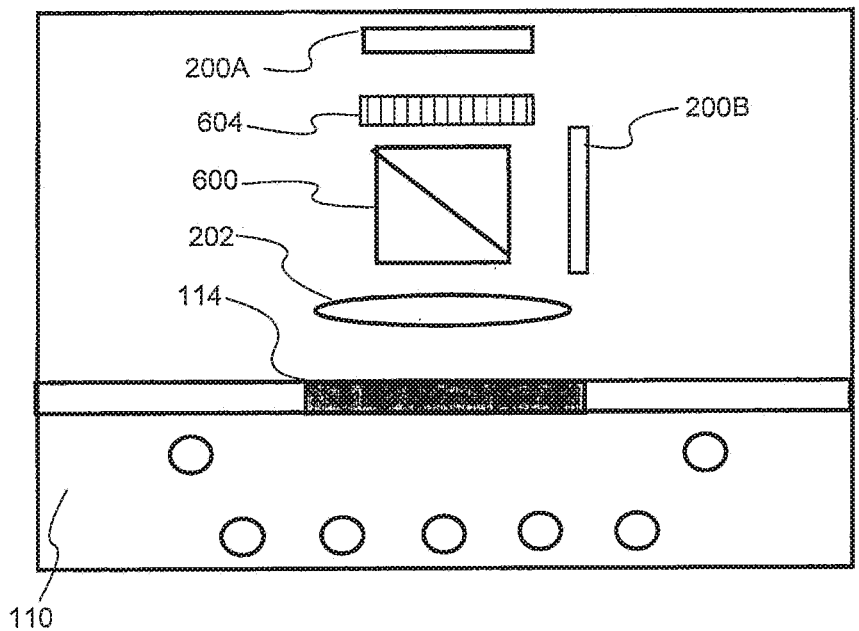
FIG. 6F is a diagrammatic representation of another configuration for determining phase information of a sample under a plurality of illumination conditions, consistent with the disclosed embodiments.

According to yet another embodiment that may be implemented in the configurations of FIG. 6E and FIG. 6F, microscope 100 may include illumination assembly 110, lens 202, an optical element 604, and at least one image sensor 200. In this embodiment, optical element 604 is configured to impose some form of modulation on the light received from sample 114 and/or a fiducial marking in proximity to sample 114, as described herein. The modulation may be imposed on the phase, the frequency, the amplitude, or the polarization of the beam. In the configuration illustrated in FIG. 6E, microscope 100 may include a dynamic optical element, such as spatial light modulator (SLM) that may dynamically change the modulation. Processor 106 may use the different information caused by the dynamic optical element to determine the phase information under each illumination condition. Alternatively, in the configuration illustrated in FIG. 6F, microscope 100 may include a fixed optical element, such as phase-shift mask, beam splitter 600, first image sensor 200A, and second image sensor 200B. Processor 106 may combine information from first image sensor 200A and second image sensor 200B to determine the phase information under each illumination condition.

In one embodiment, processor 106 may determine phase information under each illumination condition independently. FIG. 7 is a flow diagram showing the process of FIG. 5 using the configuration of FIG. 6A. The process begins when processor 106 causes illumination assembly 110 to illuminate sample 114 and/or a fiducial marking in proximity to sample 114, as described herein, at a first illumination condition (block 700). Next, processor 106 may acquire an image when sample 114 is in focal-plane 204 (block 702). Then, processor 106 may cause focus actuator 104 to change the distance between image capture device 102 and sample 114 and/or a proximate fiducial marking (block 704), and acquire an additional image when sample 114 and/or a proximate fiducial marking is not in focal-plane 204 (block 706). In some embodiments, the distance between image capture device 102 and sample 114 and/or a proximate fiducial marking may constitute a distance from sample 114 and/or a proximate fiducial marking to lens 202 or image sensor 200, or a sum of the distance from lens 202 to sample 114 and/or a proximate fiducial marking and the distance from image sensor 200 to sample 114 and/or a proximate fiducial marking. Thereafter, processor 106 may determine whether there is sufficient data to determine the phase information (decision block 708). If there is insufficient data to determine the phase information, processor 106 may repeat the steps in blocks 704-708 until there is sufficient data to determine the phase information of sample 114 under the current illumination condition. The phase may be calculated using methods such as transport of intensity (TIE), error reduction algorithms, Hybrid input-output (HID), optimization algorithms such as gradient descent and others.

The example process of FIG. 7 may continue when processor 106 transforms the image captured from real space in the focal plane 204 to a Fourier space (block 710). Thereafter, processor 106 may add image data associated with the current illumination condition to a combined complex image (block 712). If processor 106 collected all of the image data associated with all of the illumination conditions and added them to the combined complex image (decision block 714), then processor 106 may transform the combined complex image into the image-plane to generate a reconstructed image of sample 114. But, if not all of the image data associated with all of the illumination conditions was collected, processor 106 may cause illumination assembly 110 to illuminate sample 114 and/or a proximate fiducial marking under another illumination condition (block 716) and then may repeat steps 702-714.

Figure 8:
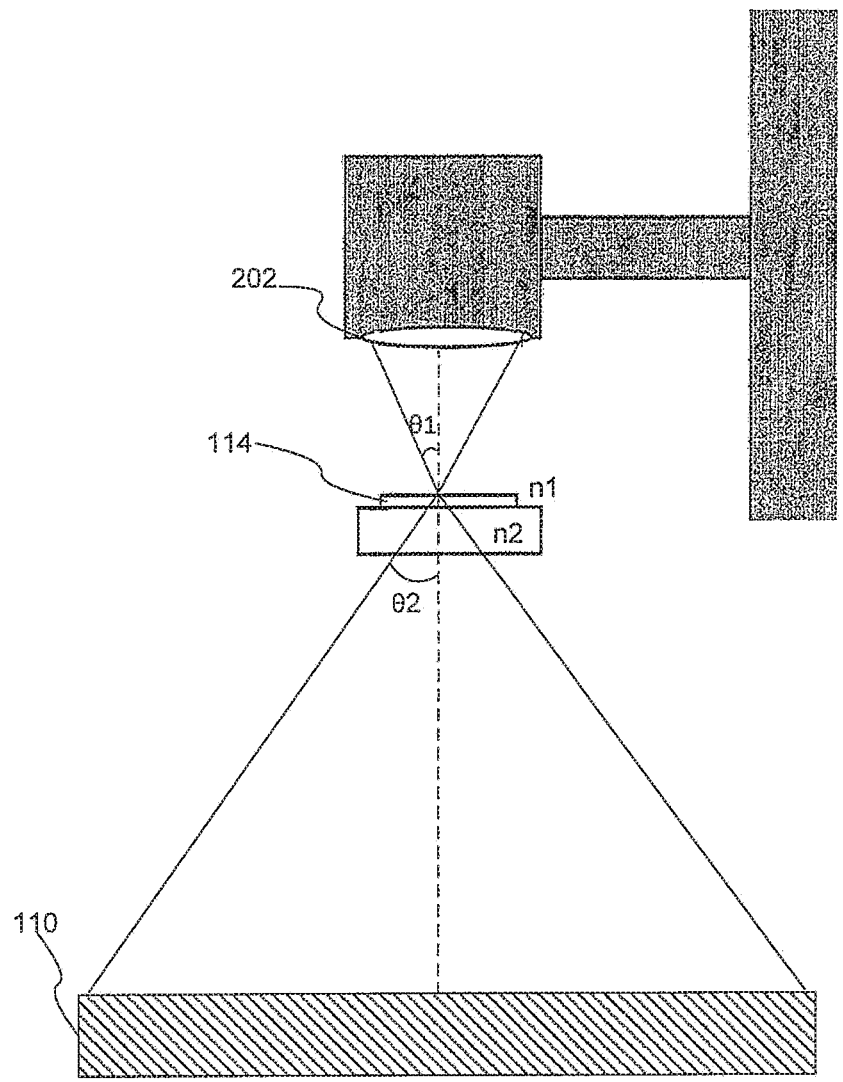
FIG. 8 is a diagrammatic representation of the numerical aperture of the microscope of FIG. 1, consistent with the disclosed embodiments.

FIG. 8 is a schematic illustration that identifies the numerical aperture (NA) of microscope 100. Consistent with the present disclosure, microscope 100 may include a lens (e.g., lens 202) with a first numerical aperture. The term "numerical aperture" refers to the medium index of refraction (e.g., $n_1$) multiplied by the sine of the maximal angle (e.g., $\theta_1$) formed between the optical axis of the lens and the cone of light beams over which the lens can accept light, i.e., $NA_1 = n_1 * \sin \theta_1$. For example, the first numerical aperture may be less than 1, less than 0.8, less than 0.6, less than 0.4, less than 0.2, or less than 0.1, or can be more than 1. In addition, illumination assembly 110 may illuminate sample 114 and/or a fiducial marking in proximity to sample 114, as described herein, at an incidence angle of illumination. The term "incidence angle of illumination" refers to an angle (e.g., $\theta_2$) formed between the optical axis of the lens and a light beam projected from illumination assembly 110. In some embodiments, the maximal incidence angle of illumination represents a second numerical aperture, i.e., $NA_2 = n_2 * \sin \text{Max } \theta_2$, which is at least 1.5 times the first numerical aperture. For example, the second numerical aperture may be more than $2 \times NA_1$, more than $2.5 \times NA_1$, more than $3.5 \times NA_1$, or more than $5 \times NA_1$.

Figure 9A:
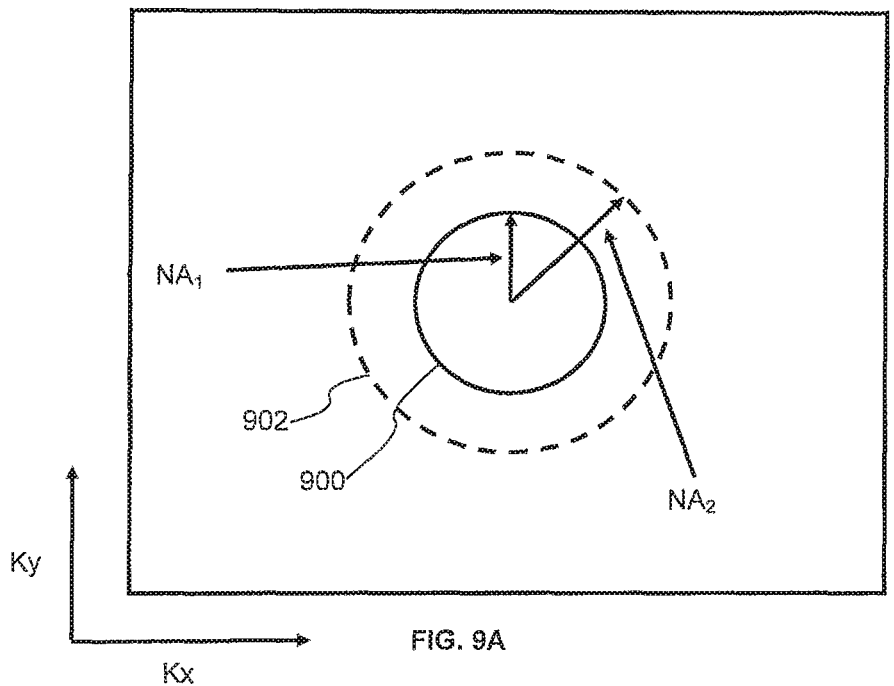
FIG. 9A is an illustration in Fourier-plane of image data acquired under a single illumination condition, consistent with the disclosed embodiments.
Figure 9B:
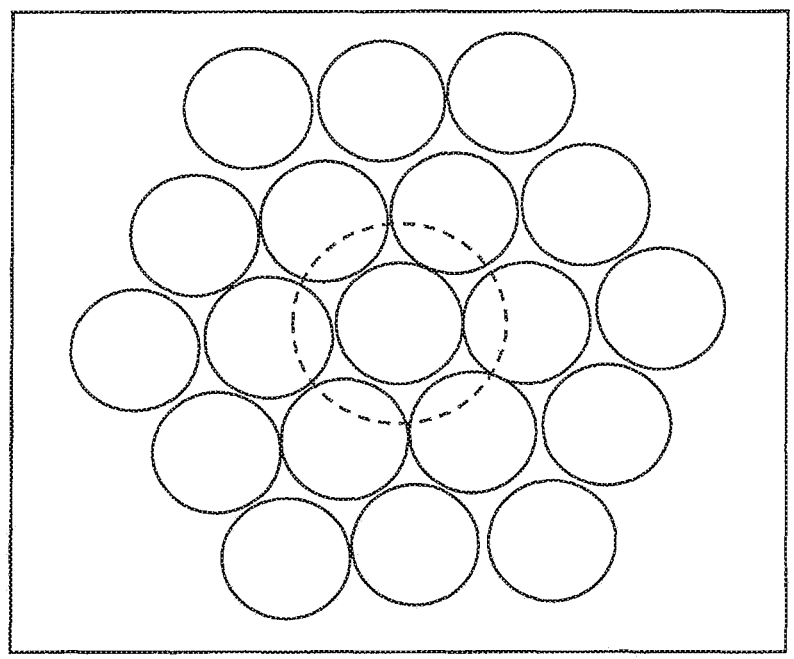
FIG. 9B is an illustration in Fourier-plane of image data acquired under a plurality of different illumination conditions, consistent with the disclosed embodiments.

FIG. 9A and FIG. 9B depict two schematic illustrations in Fourier-plane. Specifically, FIG. 9A is an illustration in Fourier-plane of image data acquired under a single illumination condition, and FIG. 9B is an illustration in Fourier-plane of image data acquired under a plurality of different illumination conditions. The illustration of FIG. 9A includes an image in Fourier-plane with a first circular area 900 in Fourier-plane whose radius is equal to $NA_1$ and a second theoretical circular area 902 whose radius is equal to $NA_2$. As shown in the figure, the radius of second circular area 902 is at least 1.5 times the radius of first circular area 900. First circular area 900 is associated with image data of sample 114 and/or a fiducial marking in proximity to sample 114, as described herein, when the illumination angle equals to 0 degrees. In one embodiment, the non-iterative process of generating the reconstructed image includes using image data associated with a single illumination condition for each point in the combined complex image. FIG. 9B illustrates this embodiment. Specifically, FIG. 9B depicts a plurality of circles in Fourier-plane. Each circle represents a point in the combined complex image and is associated with image data acquired under a single illumination condition. For example, each circle in FIG. 9B is associated with a different illumination angle. Since the radius of circular area 902 is at least 1.5 times the radius of the first circular area 900, the system in some embodiments is not limited one to a first 'order' of additional areas around area 900, but can have additional 'orders' of circular areas further away from the first circular area 900. This is important in order to achieve higher resolution of the final image. This method is not limited to increasing the numerical aperture by only a factor of 2. As described above with reference to FIG. 1, the illumination of sample 114 may result from light sources located at a surface parallel to sample 114 and/or from light sources located at a surface perpendicular to sample 114. For example, as shown in FIG. 1, light sources may be included on illumination assembly 110. Further, in some embodiments, light sources may be located at any appropriate location of microscope 100 and illuminate sample 114 at any appropriate angle. Further, light sources may be positioned on other surfaces, such as on the surface of a hemisphere or cube positioned under stage 116.

Figure 10:
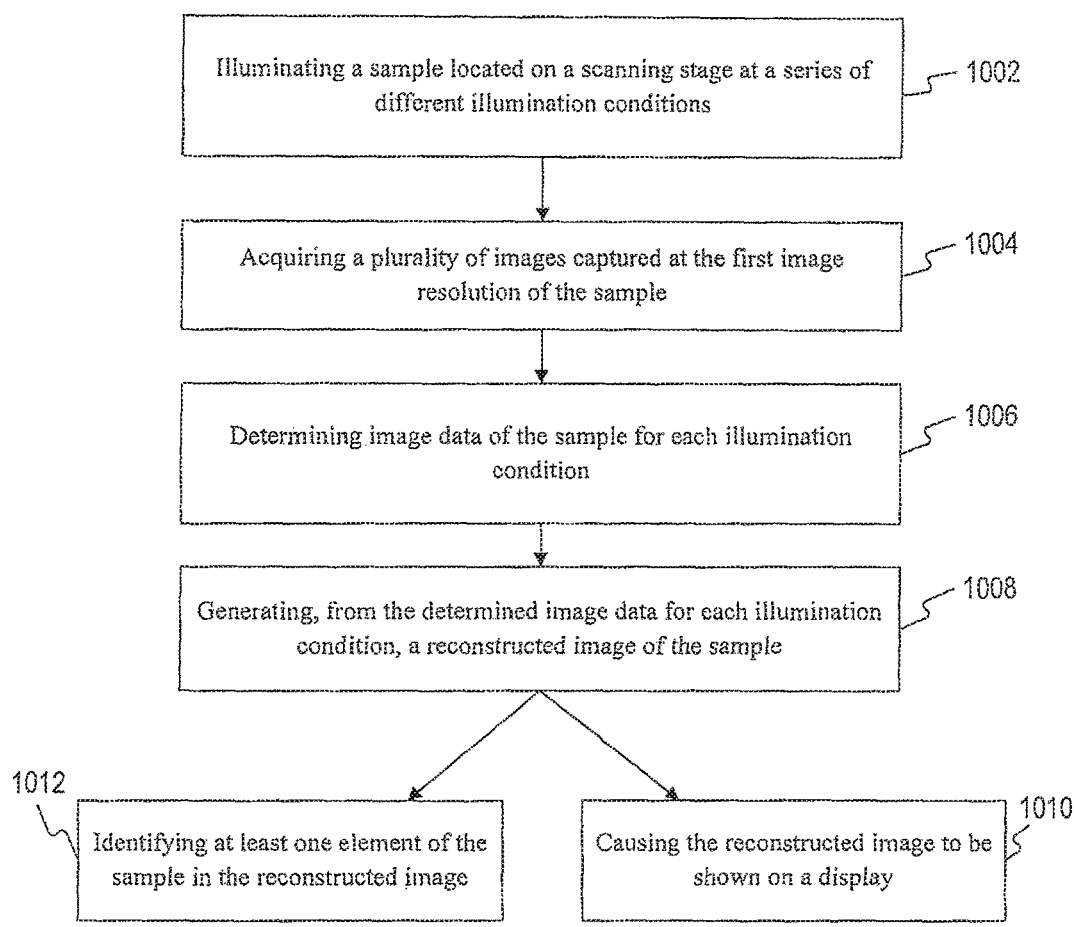
FIG. 10 is a flowchart showing an exemplary process for reconstructing an image of a sample using images acquired under a plurality of illumination conditions, consistent with the disclosed embodiments.

FIG. 10 is a flowchart showing an exemplary process 1000 for constructing a high-resolution image of sample 114 using image information acquired under a plurality of different illumination conditions. At step 1002, processor 106 may cause the illumination assembly to illuminate sample 114 at a series of different illumination conditions. As described above, the illumination conditions may include at least one of: different illumination angles, different illumination patterns, different wavelengths, or a combination thereof. At step 1004, processor 106 may acquire from image capture device 102 a plurality of images of sample 114, and/or a fiducial marking in proximity to sample 114, as described herein, and the plurality of images may include at least one image for each illumination condition. In some embodiments, the acquired images are captured at an image resolution higher than 12 megapixels with a pixel size smaller than 2 micrometers in both the horizontal and vertical dimensions High resolution sensors with small pixel sizes are low cost and lead to a large field of view, but require significant effort in working with low signal to noise ratios (a result of the small pixel size) and optimization of speed due to the high memory bandwidths and large fields of view. However our method is capable of operating with such sensors whereas other methods cannot.

At step 1006, processor 106 may determine, from the at least one image, image data of sample 114 and/or a proximate fiducial marking for each illumination condition. In some embodiments, in order to determine the image data of sample 114 and/or a proximate fiducial marking for each illumination condition, processor 106 may transform the at least one image from a real space to a Fourier space, aggregate the image data of the sample in the Fourier-space to form a combined complex image, and transform the combined complex image data back to the image space to generate the reconstructed image of sample 114. Consistent with some embodiments, determining image data of sample 114 and/or a proximate fiducial marking for each illumination condition may include determining phase information of sample 114 and/or a proximate fiducial marking under each illumination condition independently. As discussed above with reference to FIGS. 6A-6F, determining the phase information under each illumination condition may be implemented using different configurations of microscope 100.

In a first embodiment, processor 106 may acquire, from image capture device 102, a group of first images from different focal planes for each illumination condition and determine, from the group of first images, phase information under each illumination condition independently. In a second embodiment, processor 106 may acquire, from first image sensor 200A, a first image for each illumination condition; acquire, from second image sensor 200B, a second image different from the first image for each illumination condition; and combine information from the first image and the second image to determine phase information under each illumination condition independently. In a third embodiment, processor 106 may identify, for each illumination condition, an interference pattern between the first and second light beams and determine, from the interference pattern, phase information associated with each illumination condition independently. In a fourth embodiment, processor 106 may acquire, for each illumination condition, a first image from first image sensor 200A, and a second image from second image sensor 200B, wherein the second image is modulated differently from the first image; and combine information from the first image and the second image to determine phase information under each illumination condition.

At step 1008, processor 106 may generate, from the determined image data for each illumination condition, a reconstructed image of sample 114, where the reconstructed image has a second image resolution higher than the first image resolution. In some embodiments, processor 106 may generate the reconstructed image in a non-iterative process. The term "generate a reconstructed image in a non-iterative process" refers to a process in which the reconstructed image is not compared to the acquired images nor are the acquired images compared to themselves. The non-iterative process may include using image data associated with a single illumination condition for each point in the combined complex image, as depicted in FIG. 9. In order to reconstruct an image in a non-iterative process, processor 106 may determine the intensity and phase information of sample 114 and/or a proximate fiducial marking for each illumination condition. Thereafter, processor 106 may use the intensity and phase information to organize all of the pieces of the puzzle (i.e., the image data determined under each illumination condition) in their place. As one skilled in art would recognize, using this non-iterative process enables one to decrease the computation time needed to reconstruct the high-resolution image. It is possible, but not mandatory, that determining the phase information or other information for each illumination condition independently will be done using an iterative process. However, generating the final high resolution image from the information determined from the multiple illumination conditions will be done in a non-iterative process. In this case the overlap between regions in Fourier space can still be reduced or eliminated.

After processor 106 generates the reconstructed image of sample 114, it may cause the reconstructed image to be shown on a display (step 1010) or identify at least one element of sample 114 in the reconstructed image (step 1012). In some embodiments, processor 106 may confirm the quality of the reconstructed image before using it. For example, processor 106 may generate the reconstructed image using a first set of constructing parameters, and determine that the reconstructed image is not in a desired quality. In one example, the determination that reconstructed image is not in the desired quality is based on a level of sharpness of the reconstructed image or parts of it, or a comparison with expected or known results based on prior knowledge. Thereafter, processor 106 may generate a second reconstructed image using a second set of constructing parameters. In addition, processor 106 may acquire another set of images of sample 114 and/or a proximate fiducial marking after changing the focus of microscope 100, as described above with reference to FIG. 4.

In many detection systems, any prior knowledge of the sample can greatly improve the performance of the system in terms of the quality of the results (e.g., images acquired) or the computation time (e.g., time required to reconstruct high resolution images). In some embodiments, a microscope may make use of a fiducial marking with known features and make use of the fiducial marking to increase the efficiency or effectiveness of image collection and/or reconstruction processes. Accordingly, any computational scheme that is used to acquire images, improve image resolution, or analyze image data from sample 114 can use knowledge of the fiducial marking (e.g., its pattern, color, shape, intensity, phase, other feature, or a combination thereof). A fiducial marking may be disposed in any useful location. For example, a fiducial marking may be disposed on a surface of a microscope slide, cover slip, or stage. In some instances, a fiducial marking may be disposed beneath sample 114 (e.g., between sample 114 and one or more illumination sources). In other instances, a fiducial marking may be disposed above sample 114 (e.g., between sample 114 and lens 202, image sensor 200, or image capture device 102). In other cases, a fiducial marking may be placed next to sample 114 (e.g., in or approximately in the plane of sample 114). For systems including a fiducial marking comprising a known pattern, when a parameter or parameters in the system is determined (for example, but not limited to, focal length and translation of some part of the system), a parameter or parameters may be adjusted in such a way that a computed pattern corresponding to the fiducial marking matches the known pattern. These parameters may also be readily optimized to sample 114.

In some embodiments, the detection system for a system including a fiducial marking may be consistent with the microscope systems described herein. The system may comprise sample 114, image capture device 102, and illumination assembly 110. Additionally, sample 114 may be in proximity to a fiducial marking. As used herein, the phrase "in proximity to" and the corresponding descriptor "proximate to" implies that two or more components are within a small distance from one another. For example, a fiducial marking may be disposed above or below sample 114 (e.g., directly above or below, or separated by one or more components of the system such as a coverslip, microscope slide, fluid, or refractive index matching material). Similarly, a fiducial marking may be located in the same plane or approximately the same plane as sample 114 and may be, for example, disposed adjacent to sample 114. In some embodiments, a fiducial marking and sample 114 may both be disposed on the same side of a microscope slide or stage.

A fiducial marking may comprise any useful material including a reflective or refractive material. A fiducial marking may be of any useful color, shape, intensity, thickness, texture, and configuration. In some embodiments, a fiducial marking is projected onto a component of the system, e.g., as described herein.

In some embodiments, a fiducial marker comprises features within a range from about 0.1 to 10 times (e.g., 0.1 to 5 times, 0.1 to 2 times, 0.2 to 5 times, 0.2 to 2 times, 0.5 to 2 times, 0.5 to 5 times, 0.5 to 10 times, 2 to 5 times, or 2 to 10 times) a size of the smallest features of a sample of interest. For example, a fiducial marker may comprise a line of a thickness that is 0.1 times the thickness of the smallest feature of a sample of interest (e.g., a cell).

In some cases, a system may include more than one fiducial marking. For example, a system may include a plurality of fiducial markings in different planes (e.g., a fiducial marking disposed below sample 114 and a fiducial marking disposed above 114, or a fiducial marking disposed in the same plane as sample 114 and a fiducial marking disposed above or below sample 114). In another example, a system may include a plurality of fiducial markings in the same plane. In some embodiments, a fiducial marking may comprise a reference pattern (e.g., a pattern with one or more features known to a user, processor 106, and/or another component of a microscope system). A reference pattern may comprise a unit that repeats one or more times, and may comprise a predetermined spatial frequency. For example, a fiducial marking may include a series of parallel lines, a grid, or any other useful pattern.

In an exemplary system, sample 114 and a fiducial marking comprising a known pattern are illuminated under a plurality of different illumination conditions, consistent with embodiments described herein, and a series of low resolution images may be acquired including all or a portion of sample 114 and all or a portion of the fiducial marking. The system may produce a high resolution image based on the information from the low resolution images using a reconstruction process, for example, using the reconstruction process described herein. This process may be an iterative or non-iterative process using prior knowledge of the known pattern of the fiducial marking. For example, the computed high resolution image of the known pattern may be compared to a known (e.g., previously determined) high resolution image of the known pattern between iterations.

Figure 11:
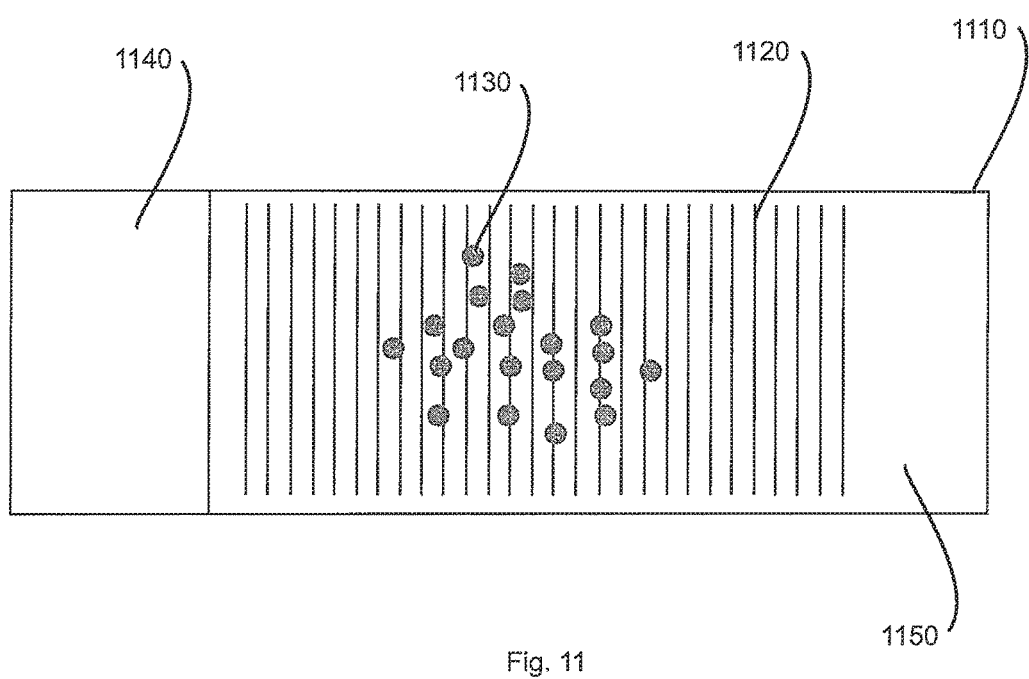
FIG. 11 is a diagrammatic representation of an exemplary sample on top of a reference pattern on a microscope slide, consistent with the disclosed embodiments.

FIG. 11 shows an exemplary sample on a slide showing a fiducial marking comprising a reference pattern in accordance with some embodiments. As shown in FIG. 11, fiducial marking 1120 may be disposed on microscope slide 1110 before sample 1130 is placed on slide 1110. In some cases, fiducial marking 1120 is projected on slide 1110 in proximity to, beneath, above, or adjacent to sample 1130 using an optical projection system. The reference pattern of fiducial marking 1120 may be a diffraction pattern caused by the interaction between a coherent or semi-coherent light source and a diffraction mask. In other cases, fiducial marking 1120 may comprise material deposited on slide 1110. The reference pattern may have specific properties in or on multiple directions or orientations such that it will be possible to efficiently manipulate or locate the pattern in Fourier space. The reference pattern may be designed to scatter light into the numerical aperture of the objective (i.e., the "brightfield"), outside of the numerical objective (i.e., the "darkfield") or both. Slide 1110 may further include identification area 1140 for placing a patient or sample identifier such as a barcode as well as transparent area 1150.

Figure 12A:
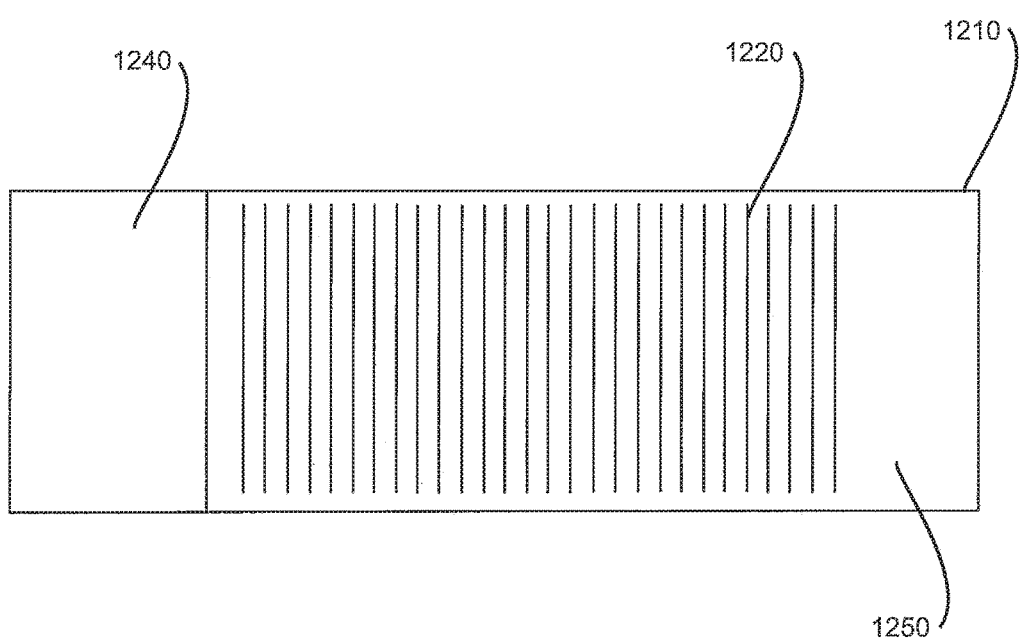
FIG. 12A is a diagrammatic representation of a one-dimensional reference pattern, consistent with the disclosed embodiments.
Figure 12B:
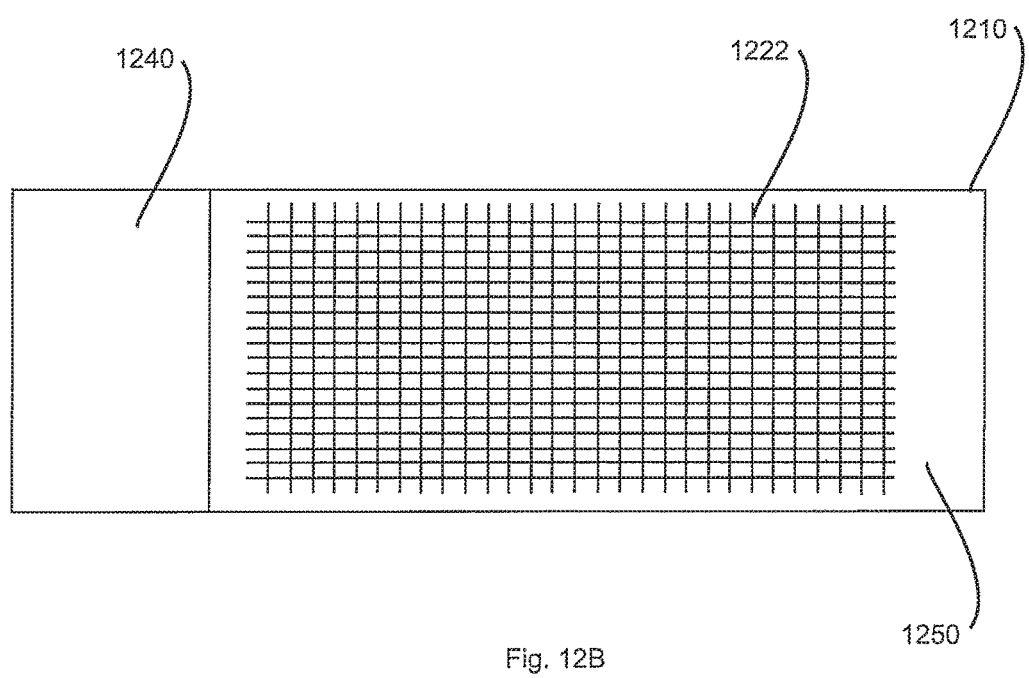
FIG. 12B is a diagrammatic representation of a two-dimensional reference pattern, consistent with the disclosed embodiments.
Figure 12C:
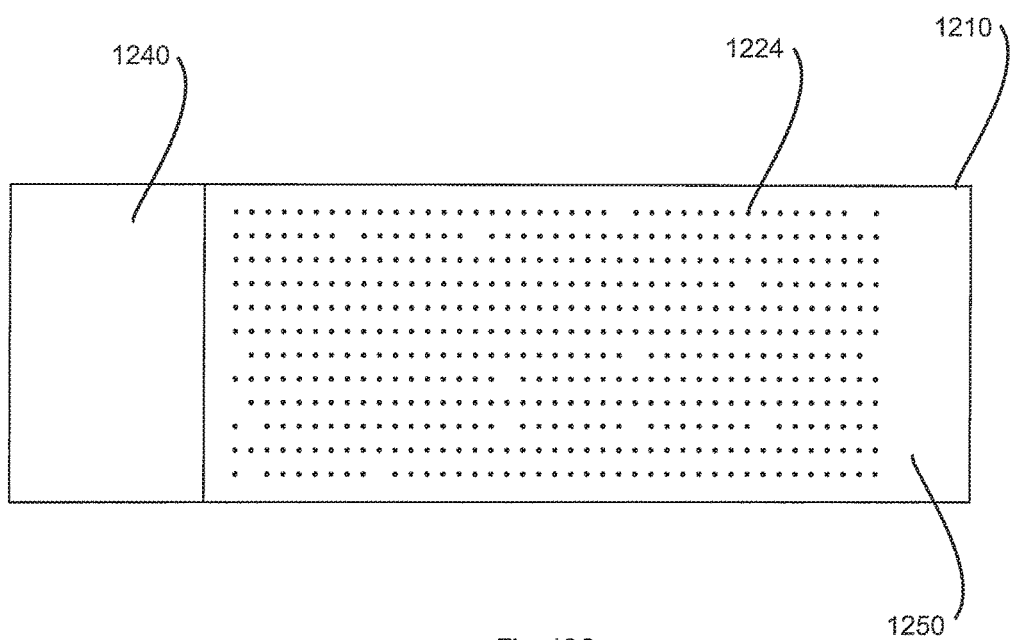
FIG. 12C is a diagrammatic representation of a two-dimensional reference pattern of delta functions, consistent with the disclosed embodiments.

FIGS. 12A-12C show exemplary fiducial markings comprising reference patterns on slide 1210 in accordance with some embodiments. As shown in FIG. 12A, the reference pattern may be a one dimensional (1-D) periodic pattern (1220). As shown in FIG. 12B, the reference pattern may be a two dimensional (2-D) periodic pattern (1222). The periodic pattern may or may not have the same spatial frequency in multiple axes. The reference pattern may affect a physical property of the light from illumination assembly 110 including but not limited to the intensity (e.g., absorption or diffraction) or the phase (e.g., phase retardation). The reference pattern may be such that each field of view includes a single delta function (e.g., a single dot with dimensions comparable to those of a sample of interest or a computed spatial resolution) or a plurality of delta functions (e.g., many dots). FIG. 12C shows a reference pattern on with an array of delta functions (1224) in accordance with some embodiments. The reference pattern may be comprised of a single or a plurality of delta functions organized in a specific geometric arrangement or semi-randomly distributed. As in FIG. 11, slide 1210 may further include identification area 1240 for placing a patient or sample identifier such as a barcode as well as transparent area 1250.

Several methods in the field of computational imaging may be used in order to produce a high resolution image of a sample from a series of low-resolution images taken under different illumination conditions. One of these methods is, for example, ptychography, as described above. These methods may use an iterative process in order to compute the high resolution image in such a way that the reconstructed image (which may, for example, include reconstructed phase and/or intensity information) in each iteration may be compared to the pre-iteration high resolution image. In such an example, the difference between the pre-iteration high resolution image and the reconstructed image in that particular iteration may serve as a convergence condition.

An exemplary iterative process using a fiducial marking comprising a reference pattern is as follows. For example, the reference pattern may be periodic with a period $K_o$. Using a reconstruction process described herein, the convergence criteria may be met and the high resolution image considered final when the Fourier transform of the high resolution image consists of a sufficient signal around a pre-determined $K_o$. Additionally, using a known frequency $K_o$, an algorithm (e.g., the convex relaxation algorithm) may be improved or accelerated by assuming the image will include the known frequency.

In another example, the known pattern may be used as a "stopping condition" for iterative optimization in image space. Such an example may use computer vision to recognize the reference pattern and optimize in image space for the reference pattern. This may have the added benefit of making the recognized pattern easier to digitally remove. In similar methods, the reference pattern may be reconstructed in a basis that is not in the image space or the Fourier space. This basis may include one whose parameters change with the imaging conditions (e.g. the focus).

Rather than using the reference pattern as a "stopping condition" in, e.g., an iterative method, prior knowledge of the reference pattern may be inserted into a cost/loss function in, for example, a gradient descent method, e.g., in a regularization term of the process. The reference pattern may also be used as an initial guess for the image reconstruction with or without a low resolution image. In some cases, the reference pattern may be used a check that the local minimum optimized from the low-resolution image is the global convergence minimum. The reference pattern may be used as a regularization term in methods such as error reduction; phase retrieval (e.g., Gerchberg-Saxton); Fresnel propagation, transport of intensity, etc., in embodiments with multiple focal planes; and/or to generally assist regularization or optimization methods.

In another example, the reference pattern is disposed in a different focal plane from the sample. For instance, the reference pattern may be on one side of a coverslip while the sample is disposed between the coverslip and a stage. The knowledge of the reference pattern's disposition in another focal plane can be used to reconstruct a computational z-stack (e.g., digital refocusing) because significant information is available in an out-of-focus plane.

In other embodiments, the reconstruction process may be non-iterative. Making use of such a reconstruction process may provide the benefit of decreasing the computation time necessary to achieve a high resolution image. A non-iterative reconstruction process may also be preferential to an iterative process because iterative processes may not always be stable and may not converge. In some embodiments, the detection system may be consistent with the microscope described herein. The system may comprise sample 114, image capture device 102, and illumination assembly 110. Consistent with embodiments described herein, a series of low resolution images may be acquired at a plurality of illumination conditions. The system may produce a high resolution image based on the information from the low resolution images using a reconstruction process, for example using the reconstruction process described herein.

In an example embodiment, the plurality of illumination conditions may comprise different illumination angles. The system may then produce the high resolution image by locating in Fourier space overlapping or non-overlapping regions corresponding to the different illumination angles, consistent with embodiments described herein. The system may directly measure or calculate the intensity and/or phase for each or a fraction of the acquired low resolution image or images (e.g., based upon a reference pattern). Consistent with embodiments described herein, for example, with respect to the method of FIG. 7 using configuration of FIG. 6A, the system may acquire a series of low resolution images in different focal planes for a plurality of illumination angles. The system may then compute the complex image for such an illumination angle, consistent with the reconstruction process described herein.

An example embodiment for non-iteratively calculating the phase may include using a coherent illumination source resulting in, for example, a detected interference image from which a complex image may be calculated. For example, an interference image may be created using a reference illumination and a probe illumination resulting in an interference pattern according to the configurations of FIGS. 6B-6F. The reference illumination and the probe illumination may be, for example, scattered from or transmitted through the sample. In another example, a plurality of coherent, incoherent, or semi-coherent illumination sources may be located symmetrically with respect to the sample such that the sample may be illuminated in the same angle but in opposite directions from both sources. The phase may then be calculated from spatial symmetry.

Another example embodiment may include wherein the reference pattern of, for example, FIG. 11 or any one of FIGS. 12A-12C is or comprises a diffraction grating (e.g., a diffraction grating engraved on a surface of a slide or stage supporting a sample). The groove density may be designed so that the first order of diffraction scatters at an angle larger than the angle corresponding to the numerical aperture of the objective lens. In such a configuration, plane wave illuminations starting from an angle perpendicular to the sample up to an angle corresponding to the numerical aperture plus the maximal significant diffraction order from the grating may effectively result in a combination of brightfield and dark field illumination angles. Such a combination may be used to compute in an iterative (or alternatively a non-iterative) process both intensity and phase information of the light scattered by the sample. An alternative embodiment may be to implement the previous scheme by imaging the grating onto the vicinity of the sample plane thereby avoiding the necessity of engraving it on the sample. In such an embodiment, the varying illumination angles may also pass through the illumination imaging system. Both of the embodiments described above, may be implemented with arbitrary reference patters (e.g., not necessarily a grating) and combined with multi-angle illumination.

A fiducial marking comprising a reference pattern may be used to reference the spatial position of a feature of interest of a sample. For instance, the reference pattern may be used to identify the amount of lateral shift between one or more image features present in a first image of the sample and a corresponding one or more image features present in a second image (e.g., to aid in step 410 of FIG. 4). A fiducial marking comprising a reference pattern may be used to assist in calibration of a sensor's optical alignment, including calibration of one sensor relative to another in an embodiment with a plurality of sensors (e.g., in a system employing two or more image sensors or cameras). A fiducial marking comprising a reference pattern may be used to calibrate image intensity using prior knowledge of the scattering from the pattern in different illumination angles. In some embodiments, the reference pattern may be in a different focal plane from the sample. The pattern may be on the non-sample side of a slide, on either side of a coverslip, etc. In such an embodiment, the pattern in the out-of-focus place is known, and this information can be used to digitally refocus an image (e.g., a computational z-stack). The reference pattern can also be used in a regularization term to assist or enable convergence during reconstruction (via, e.g., Fresnel propagation or transport of intensity) of phase using refocusing (e.g., z stack) or multiple sensors in different focal planes.

Figure 13:
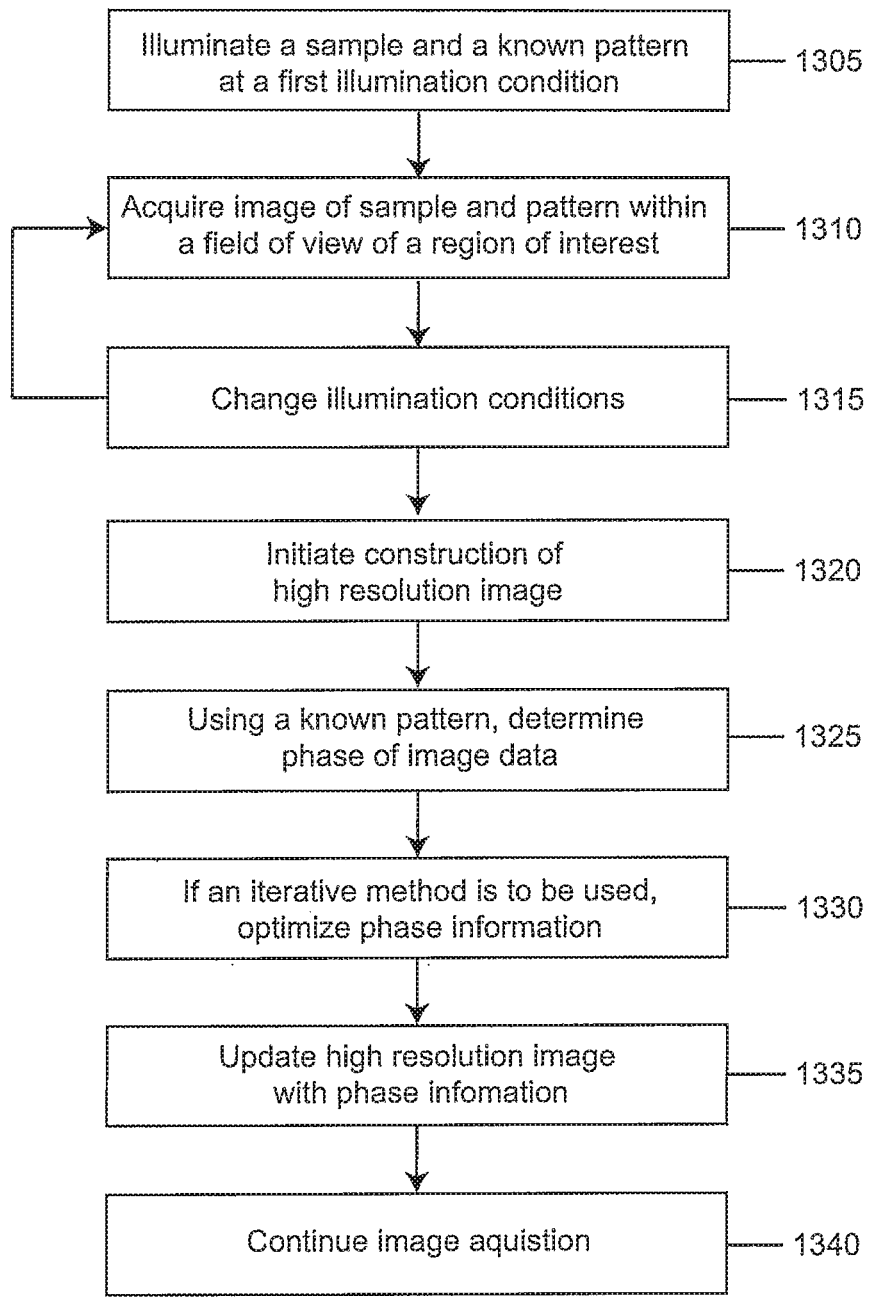
FIG. 13 is a flowchart showing an exemplary process for reconstructing an image using a fiducial marking, consistent with the disclosed embodiments.

FIG. 13 is a flowchart showing an exemplary method 1300 of reconstructing an image using a fiducial marking. At a step 1305, the sample and a fiducial marking are illuminated at a first illumination condition as described herein. At a step 1310, an image of the sample and a fiducial marking are acquired with a field of view of a region of interest, as described herein. At a step 1315, illumination conditions may be changed as described herein. As shown, steps 1310 and 1315 may be repeated as necessary, as described herein. At a step 1320, construction of a high resolution image is initiated. At a step 1325, the phase of the image data is determined using a fiducial marking, as described herein. At a step 1330, the phase information may be optimized based on an iterative method, as described herein. At a step 1335, the high resolution image is updated with the appropriate phase information. At a step 1340, image acquisition may be continued, as described herein.

While FIG. 13 shows a method of reconstructing an image using a fiducial marking, a person of ordinary skill in the art will recognize many adaptations and variations. For example, the some of the steps can be deleted, some of the steps repeated, and the steps can be performed in any order.

Computer Control Systems

In some embodiments, the platforms, systems, media, and methods described herein include a digital processing device, or use of the same. In further embodiments, the digital processing device includes one or more hardware central processing units (CPUs), general purpose graphics processing units (GPGPUs), or field programmable gate arrays (FPGAs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 14:
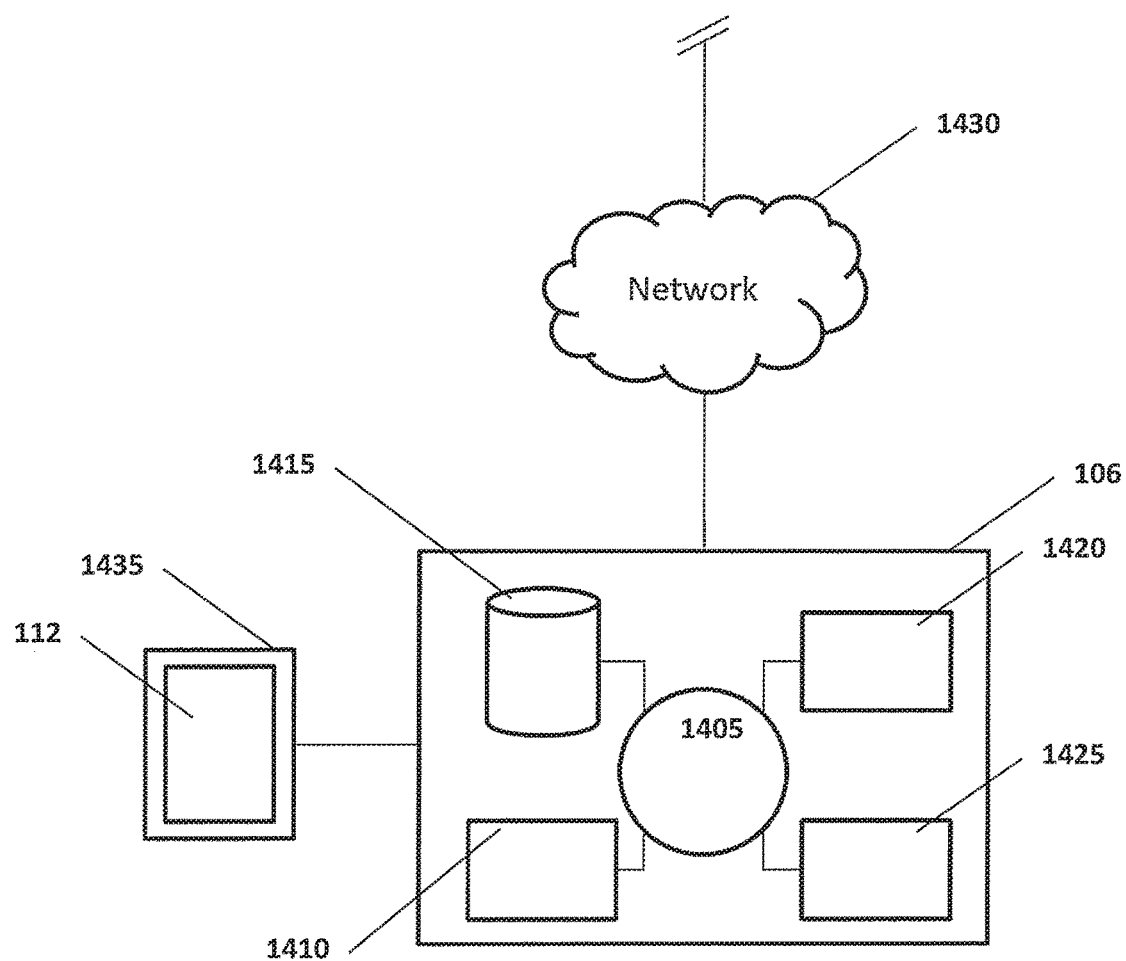
FIG. 14 shows a computer control system that is programmed or otherwise configured to implement methods provided herein.

Referring to FIG. 14, in a particular embodiment, an exemplary digital processing device 106 is programmed or otherwise configured to an imaging device as described herein. The device 106 can regulate various aspects of the microscope of the present disclosure, such as, for example, performing processing steps. In this embodiment, the digital processing device 106 includes a central processing unit (CPU, also "computer processor" herein) 1405, which can be a single core or multi core processor, or a plurality of computer processors for parallel processing. The digital processing device 106 also includes memory or memory location 1410 (e.g., random-access memory, read-only memory, flash memory), electronic storage unit 1415 (e.g., hard disk), communication interface 1420 (e.g., network adapter) for communicating with one or more other systems, and peripheral devices 1425, such as cache, other memory, data storage and/or electronic display adapters. The memory 1410, storage unit 1415, interface 1420 and peripheral devices 1425 are in communication with the CPU 1405 through a communication bus (solid lines), such as a motherboard. The storage unit 1415 can be a data storage unit (or data repository) for storing data. The digital processing device 106 can be operatively coupled to a computer network ("network") 1430 with the aid of the communication interface 1420. The network 1430 can be the Internet, an internet and/or extranet, or an intranet and/or extranet that is in communication with the Internet. The network 1430 in some cases is a telecommunication and/or data network. The network 1430 can include one or more computer servers, which can enable distributed computing, such as cloud computing. The network 1430, in some cases with the aid of the device 1401, can implement a peer-to-peer network, which may enable devices coupled to the device 106 to behave as a client or a server.

Continuing to refer to FIG. 14, the CPU 1405 can execute a sequence of machine-readable instructions, which can be embodied in a program or software. The instructions may be stored in a memory location, such as the memory 1410. The instructions can be directed to the CPU 1405, which can subsequently program or otherwise configure the CPU 1405 to implement methods of the present disclosure. Examples of operations performed by the CPU 1405 can include fetch, decode, execute, and write back. The CPU 1405 can be part of a circuit, such as an integrated circuit. One or more other components of the device 106 can be included in the circuit. In some cases, the circuit is an application specific integrated circuit (ASIC) or a field programmable gate array (FPGA).

Continuing to refer to FIG. 14, the storage unit 1415 can store files, such as drivers, libraries and saved programs. The storage unit 1415 can store user data, e.g., user preferences and user programs. The digital processing device 106 in some cases can include one or more additional data storage units that are external, such as located on a remote server that is in communication through an intranet or the Internet.

Continuing to refer to FIG. 14, the digital processing device 106 can communicate with one or more remote computer systems through the network 1430. For instance, the device 106 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

The computer system 106 can include or be in communication with an electronic display 1435 that comprises a user interface (UI) 112 for providing, for example, access to high or low resolution images, access raw or reconstructed images, control of microscope 100, etc. Examples of UI's include, without limitation, a graphical user interface (GUI) and web-based user interface.

Methods as described herein can be implemented by way of machine (e.g., computer processor) executable code stored on an electronic storage location of the digital processing device 1401, such as, for example, on the memory 1410 or electronic storage unit 1415. The machine executable or machine readable code can be provided in the form of software. During use, the code can be executed by the computer processor 1405. In some cases, the code can be retrieved from the storage unit 1415 and stored on the memory 1410 for ready access by the computer processor 1405. In some situations, the electronic storage unit 1415 can be precluded, and machine-executable instructions are stored on memory 1410. Memory 108 as embodied herein may comprise memory 1410 and/or electronic storage unit 1415.

Non-transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Methods and systems of the present disclosure can be implemented by way of one or more algorithms. An algorithm can be implemented by way of software upon execution by the central processing unit 1105. The algorithm can, for example, construct a high resolution image, collect images according to user-determined instructions, receive or transmit data to one or more computer systems, etc.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed routines may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A microscope for generating a high resolution image of a sample, said microscope comprising:
an illumination assembly;
an image capture device;
a fiducial marker imaged with said image capture device; and
a processor coupled to said illumination assembly and said image capture device, said processor configured with instructions to:
acquire a plurality of images under a plurality of different illumination conditions, wherein said sample and said fiducial marker are present within said plurality of images, wherein at least one of said plurality of images is a brightfield image comprising said fiducial marker; and
reconstruct said high resolution image of said sample in response to said fiducial marker and said plurality of images, wherein said brightfield image comprising said fiducial marker is used in said reconstruction and wherein said high resolution image of said sample is a brightfield image.

2. The microscope of claim 1, wherein said plurality of images each comprises a resolution and said high resolution image comprises a resolution greater than said resolution of said each said plurality of images.

3. The microscope of claim 1, wherein said fiducial marker comprises a predetermined pattern.

4. The microscope of claim 1, wherein said fiducial marker comprises a predetermined periodic pattern comprising a predetermined spatial frequency.

5. The microscope of claim 1, wherein said fiducial marker comprises a predetermined spatial frequency and wherein said processor is configured with instructions to reconstruct said high resolution image in response to said predetermined spatial frequency of said fiducial marker.

6. The microscope of claim 1, wherein said processor is configured with instructions to reconstruct said high resolution image in response to a frequency of said fiducial marker and optionally wherein said processor is configured with instructions to reconstruct said high resolution image in response to a plurality of frequencies of said fiducial marker and optionally wherein said processor is configured with instructions to reconstruct said high resolution image in response to said plurality of frequencies of said fiducial marker in each of said plurality of images.

7. The microscope of claim 1, wherein said processor is configured with instructions to reconstruct said high resolution image in response to a phase of said fiducial marker in said reconstructed image and optionally wherein said processor is configured with instructions to reconstruct said high resolution image in response to a phase difference between a phase of said fiducial marker and a phase of said fiducial marker in said reconstructed image.

8. The microscope of claim 1, wherein said fiducial marker is disposed between said sample and an illumination source.

9. The microscope of claim 1, wherein said fiducial marker is disposed between said sample and said image capture device and optionally wherein said fiducial marker is located between said sample and an objective lens of said illumination device.

10. The microscope of claim 1, wherein said fiducial marker comprises a physical object disposed adjacent to said sample.

11. The microscope of claim 1, wherein said sample and said fiducial marker are disposed on a microscope slide.

12. The microscope of claim 1, wherein said fiducial marker has been fabricated on a microscope slide.

13. The microscope of claim 1, wherein said fiducial marker is located on a microscope slide supporting said sample.

14. The microscope of claim 1, wherein said fiducial marker is disposed on a coverslip.

15. The microscope of claim 1, wherein said processor is configured with instructions to:
determine an attribute value of said fiducial marker in said plurality of images; and
generate a reconstruction parameter if said attribute value is outside a predetermined range.

16. The microscope of claim 15, wherein said attribute value is selected from the group consisting of a phase value, a frequency value, and an intensity value.

17. The microscope of claim 15, wherein said attribute value corresponds to a presence or weight of a frequency of said pattern in said high resolution image.

18. The microscope of claim 15, wherein said attribute value of said fiducial marker is obtained by performing a transformation to the frequency domain on one or more of said plurality of images.

19. The microscope of claim 15, wherein said processor is configured with instructions to: (i) generate a first reconstructed image using said reconstruction parameter, (ii) determine that said first reconstructed image is not of a desired quality, (iii) adjust said reconstruction parameter, and (iv) generate a second reconstructed image.

20. The microscope of claim 19, wherein step (ii) is based on a level of sharpness of said first reconstructed image.

21. The microscope of claim 1, wherein said plurality different illumination conditions comprise conditions selected from the group consisting of different illumination angles, different illumination wavelengths, different illumination patterns, different illumination durations, different illumination intensities, and different illumination positions.

22. The microscope of claim 1, wherein said processor is configured to reconstruct said high resolution image from said plurality of images without iterations.

23. The microscope of claim 1, wherein said processor is configured to reconstruct said high resolution image from said plurality of images with iterations.

* * * * *